(12) United States Patent
Wood, Jr.

(10) Patent No.: US 8,337,482 B2
(45) Date of Patent: *Dec. 25, 2012

(54) SYSTEM FOR PERFUSION MANAGEMENT

(75) Inventor: Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1417 days.

This patent is subject to a terminal disclaimer.

(21) Appl. No.: 10/827,576

(22) Filed: Apr. 19, 2004

(65) Prior Publication Data

US 2005/0234399 A1    Oct. 20, 2005

Related U.S. Application Data

(63) Continuation-in-part of application No. 10/827,572, filed on Apr. 19, 2004, and a continuation-in-part of application No. 10/827,578, filed on Apr. 19, 2004, and a continuation-in-part of application No. 10/827,390, filed on Apr. 19, 2004.

(51) Int. Cl.
*A61M 25/00* (2006.01)
*A61M 37/00* (2006.01)

(52) U.S. Cl. .................. 604/528; 604/288.04; 604/523; 604/264; 604/93.01

(58) Field of Classification Search .................. 604/272, 604/187, 194–196, 239, 93.01, 264, 164.01; 600/101–183; 606/107
See application file for complete search history.

(56) References Cited

U.S. PATENT DOCUMENTS

| | | | |
|---|---|---|---|
| 3,391,697 A | 7/1968 | Greatbatch | |
| 3,821,469 A | 6/1974 | Whetstone et al. | |
| 3,837,339 A | 9/1974 | Aisenberg et al. | |
| 3,941,127 A | 3/1976 | Froning | |
| 3,983,474 A | 9/1976 | Kuipers | |
| 4,054,881 A | 10/1977 | Raab | |
| 4,119,900 A | 10/1978 | Kremnitz | |
| 4,202,349 A | 5/1980 | Jones | |
| 4,262,306 A | 4/1981 | Renner | |
| 4,267,831 A | 5/1981 | Aguilar | |
| 4,314,251 A | 2/1982 | Raab | |
| 4,317,078 A | 2/1982 | Weed et al. | |
| 4,339,953 A | 7/1982 | Iwasaki | |
| 4,367,741 A | 1/1983 | Michaels | |
| 4,396,885 A | 8/1983 | Constant | |
| 4,403,321 A | 9/1983 | Krüger | |
| 4,418,422 A | 11/1983 | Richter et al. | |
| 4,431,005 A | 2/1984 | McCormick | |
| 4,583,190 A | 4/1986 | Salb | |
| 4,585,652 A | 4/1986 | Miller et al. | |
| 4,628,928 A | 12/1986 | Lowell | |
| 4,638,798 A | 1/1987 | Shelden et al. | |
| 4,642,786 A | 2/1987 | Hansen | |
| 4,651,732 A | 3/1987 | Frederick | |

(Continued)

FOREIGN PATENT DOCUMENTS

CN    9981027.1    10/2001

(Continued)

OTHER PUBLICATIONS

U.S. Appl. No. 11/651,946, Ferren et al.

(Continued)

*Primary Examiner* — Victoria P Shumate

(57) ABSTRACT

A system for perfusion management that monitors, maintains, diagnoses, or treats perfusion deficiencies.

24 Claims, 5 Drawing Sheets

U.S. PATENT DOCUMENTS

| | | |
|---|---|---|
| 4,658,214 A | 4/1987 | Petersen |
| 4,714,460 A | 12/1987 | Calderon |
| 4,717,381 A | 1/1988 | Papantonakos |
| 4,733,661 A | 3/1988 | Palestrant |
| 4,750,488 A | 6/1988 | Wuchinich et al. |
| 4,763,667 A | 8/1988 | Manzo |
| 4,769,006 A | 9/1988 | Papantonakos |
| 4,771,772 A | 9/1988 | DeWitt |
| 4,795,434 A | 1/1989 | Kujawski |
| 4,800,898 A | 1/1989 | Hess et al. |
| 4,805,615 A | 2/1989 | Carol |
| 4,817,601 A | 4/1989 | Roth et al. |
| 4,871,351 A | 10/1989 | Feingold |
| 4,889,526 A | 12/1989 | Rauscher et al. |
| 4,905,689 A | 3/1990 | Stack et al. |
| 4,943,296 A | 7/1990 | Funakubo et al. |
| 4,944,659 A * | 7/1990 | Labbe et al. ............... 417/413.2 |
| 4,962,453 A | 10/1990 | Pong et al. |
| 4,994,071 A | 2/1991 | MacGregor |
| 5,019,372 A | 5/1991 | Folkman et al. |
| 5,031,109 A | 7/1991 | Gloton |
| 5,051,906 A | 9/1991 | Evans, Jr. et al. |
| 5,078,140 A | 1/1992 | Kwoh |
| 5,086,401 A | 2/1992 | Glassman et al. |
| 5,153,827 A | 10/1992 | Coutre et al. |
| 5,165,064 A | 11/1992 | Mattaboni |
| 5,176,638 A | 1/1993 | Don Michael |
| 5,188,111 A | 2/1993 | Yates et al. |
| 5,204,814 A | 4/1993 | Noonan et al. |
| 5,234,457 A | 8/1993 | Andersen |
| 5,269,303 A | 12/1993 | Wernicke et al. |
| 5,279,607 A | 1/1994 | Schentag et al. |
| 5,310,404 A | 5/1994 | Gyory et al. |
| 5,313,835 A | 5/1994 | Dunn |
| 5,314,451 A | 5/1994 | Mulier |
| 5,321,614 A | 6/1994 | Ashworth |
| 5,335,657 A | 8/1994 | Terry, Jr. et al. |
| 5,337,732 A | 8/1994 | Grundfest et al. |
| 5,338,625 A | 8/1994 | Bates et al. |
| 5,339,051 A | 8/1994 | Koehler et al. |
| 5,353,807 A | 10/1994 | DeMarco |
| 5,374,285 A | 12/1994 | Vaiani et al. |
| 5,381,786 A | 1/1995 | Spears |
| 5,386,741 A | 2/1995 | Rennex |
| 5,395,390 A | 3/1995 | Simon et al. |
| 5,398,670 A | 3/1995 | Ortiz et al. |
| 5,403,311 A | 4/1995 | Abele et al. |
| 5,411,551 A | 5/1995 | Winston et al. |
| 5,437,660 A | 8/1995 | Johnson et al. |
| 5,476,450 A | 12/1995 | Ruggio |
| 5,497,147 A | 3/1996 | Arms et al. |
| 5,502,638 A | 3/1996 | Takenaka |
| 5,507,287 A | 4/1996 | Palcic et al. |
| 5,522,394 A | 6/1996 | Zurbrugg |
| 5,551,953 A | 9/1996 | Lattin et al. |
| 5,554,914 A | 9/1996 | Miyazawa |
| 5,569,968 A | 10/1996 | Lal et al. |
| 5,574,347 A | 11/1996 | Neubauer |
| 5,589,932 A | 12/1996 | Garcia-Rubio et al. |
| 5,593,434 A | 1/1997 | Williams |
| 5,599,324 A | 2/1997 | McAlister et al. |
| 5,610,488 A | 3/1997 | Miyazawa |
| 5,624,398 A | 4/1997 | Smith et al. |
| 5,632,754 A | 5/1997 | Farley et al. |
| 5,643,296 A | 7/1997 | Hundertmark et al. |
| 5,662,587 A | 9/1997 | Grundfest et al. |
| 5,669,874 A | 9/1997 | Feiring |
| 5,670,329 A | 9/1997 | Oberhardt |
| 5,674,276 A | 10/1997 | Andersen et al. |
| 5,688,269 A | 11/1997 | Newton et al. |
| 5,695,457 A | 12/1997 | St. Goar et al. |
| 5,697,967 A | 12/1997 | Dinh et al. |
| 5,702,432 A | 12/1997 | Chen et al. |
| 5,705,293 A | 1/1998 | Hobson |
| 5,728,089 A | 3/1998 | Lal et al. |
| 5,735,276 A | 4/1998 | Lemelson |
| 5,737,279 A | 4/1998 | Carter |
| 5,758,298 A | 5/1998 | Guldner |
| 5,782,798 A | 7/1998 | Rise |
| 5,804,563 A | 9/1998 | Still et al. |
| 5,807,395 A | 9/1998 | Mulier et al. |
| 5,819,736 A | 10/1998 | Avny et al. |
| 5,827,190 A | 10/1998 | Palcic et al. |
| 5,830,179 A | 11/1998 | Mikus et al. |
| 5,830,207 A | 11/1998 | Leeb et al. |
| 5,831,012 A | 11/1998 | Nilsson et al. |
| 5,833,603 A | 11/1998 | Kovacs et al. |
| 5,843,139 A | 12/1998 | Goedeke et al. |
| 5,855,801 A | 1/1999 | Lin et al. |
| 5,865,754 A | 2/1999 | Sevick-Muraca et al. |
| 5,873,835 A | 2/1999 | Hastings et al. |
| 5,908,027 A | 6/1999 | Butterfield et al. |
| 5,921,982 A | 7/1999 | Lesh et al. |
| 5,947,119 A | 9/1999 | Reznick |
| 5,951,600 A | 9/1999 | Lemelson |
| 5,954,675 A | 9/1999 | Dellagatta |
| 5,964,773 A | 10/1999 | Greenstein |
| 6,004,269 A | 12/1999 | Crowley et al. |
| 6,016,449 A | 1/2000 | Fischell et al. |
| 6,019,729 A | 2/2000 | Itoigawa et al. |
| 6,022,316 A | 2/2000 | Eppstein et al. |
| 6,053,873 A | 4/2000 | Govari et al. |
| 6,086,528 A * | 7/2000 | Adair ............................ 600/104 |
| 6,102,845 A | 8/2000 | Woodard et al. |
| 6,108,597 A | 8/2000 | Kirchner et al. |
| 6,111,520 A | 8/2000 | Allen et al. |
| 6,128,538 A | 10/2000 | Fischell et al. |
| 6,134,474 A | 10/2000 | Fischell et al. |
| 6,149,603 A | 11/2000 | Parker |
| 6,159,230 A | 12/2000 | Samuels |
| 6,164,284 A | 12/2000 | Schulman et al. |
| 6,170,488 B1 | 1/2001 | Spillman, Jr. et al. |
| 6,175,757 B1 | 1/2001 | Watkins et al. |
| 6,179,789 B1 | 1/2001 | Tu et al. |
| 6,185,452 B1 | 2/2001 | Schulman et al. |
| 6,186,986 B1 | 2/2001 | Berg et al. |
| 6,187,599 B1 | 2/2001 | Asher et al. |
| 6,197,013 B1 | 3/2001 | Reed et al. |
| 6,219,577 B1 | 4/2001 | Brown, III et al. |
| 6,221,099 B1 | 4/2001 | Andersen et al. |
| 6,240,312 B1 | 5/2001 | Alfano et al. |
| 6,240,316 B1 | 5/2001 | Richmond et al. |
| 6,248,345 B1 | 6/2001 | Goldenheim et al. |
| 6,249,076 B1 | 6/2001 | Madden et al. |
| 6,255,361 B1 | 7/2001 | Rajagopalan et al. |
| 6,255,793 B1 | 7/2001 | Peless et al. |
| 6,263,245 B1 | 7/2001 | Snell |
| 6,278,379 B1 | 8/2001 | Allen et al. |
| 6,280,386 B1 | 8/2001 | Alfano et al. |
| 6,289,270 B1 | 9/2001 | Baumgarten |
| 6,295,990 B1 | 10/2001 | Lewis et al. |
| 6,296,638 B1 * | 10/2001 | Davison et al. .................. 606/41 |
| 6,322,532 B1 | 11/2001 | D'Sa et al. |
| 6,337,997 B1 | 1/2002 | Rise |
| 6,372,248 B1 | 4/2002 | Qin et al. |
| 6,383,162 B1 | 5/2002 | Sugarbaker |
| 6,384,741 B1 * | 5/2002 | O'Leary, Sr. ................. 340/937 |
| 6,385,472 B1 | 5/2002 | Hall et al. |
| 6,398,280 B1 | 6/2002 | Parker et al. |
| 6,400,980 B1 | 6/2002 | Lemelson |
| 6,402,678 B1 | 6/2002 | Fischell et al. |
| 6,409,674 B1 | 6/2002 | Brockway et al. |
| 6,417,641 B2 | 7/2002 | Peless et al. |
| 6,431,171 B1 | 8/2002 | Burton |
| 6,436,120 B1 | 8/2002 | Meglin |
| 6,442,413 B1 | 8/2002 | Silver |
| 6,450,937 B1 | 9/2002 | Mercereau et al. |
| 6,453,199 B1 | 9/2002 | Kobozev |
| 6,464,687 B1 | 10/2002 | Ishikawa et al. |
| 6,475,639 B2 | 11/2002 | Shahinpoor et al. |
| 6,490,483 B2 | 12/2002 | Willis |
| 6,491,618 B1 | 12/2002 | Ganz |
| 6,493,607 B1 | 12/2002 | Bourne et al. |
| 6,497,714 B1 | 12/2002 | Ishikawa et al. |
| 6,500,174 B1 | 12/2002 | Maguire et al. |
| 6,512,949 B1 | 1/2003 | Combs et al. |
| 6,512,950 B2 | 1/2003 | Li et al. |

| | | | | | |
|---|---|---|---|---|---|
| 6,514,237 B1 | 2/2003 | Maseda | 7,037,343 B2 | 5/2006 | Imran |
| 6,530,950 B1 | 3/2003 | Alvarado et al. | 7,039,453 B2 | 5/2006 | Mullick et al. |
| 6,547,723 B1 | 4/2003 | Ouchi | 7,042,184 B2 | 5/2006 | Oleynikov et al. |
| 6,547,825 B1 | 4/2003 | Shimizu et al. | 7,044,911 B2 | 5/2006 | Drinan et al. |
| 6,548,982 B1 | 4/2003 | Papanikolopoulos et al. | RE39,133 E | 6/2006 | Clayton et al. |
| 6,554,798 B1 | 4/2003 | Mann et al. | 7,066,180 B2 | 6/2006 | Aylsworth et al. |
| 6,575,969 B1 | 6/2003 | Rittman, III et al. | 7,083,578 B2 | 8/2006 | Lewkowicz et al. |
| 6,585,763 B1 | 7/2003 | Keilman et al. | 7,101,386 B2 | 9/2006 | Dobak, III |
| 6,591,137 B1 | 7/2003 | Fischell et al. | 7,115,109 B2 | 10/2006 | Gerdts et al. |
| 6,592,567 B1 | 7/2003 | Levin et al. | 7,118,531 B2 | 10/2006 | Krill |
| 6,597,954 B1 | 7/2003 | Pless et al. | 7,125,382 B2 | 10/2006 | Zhou et al. |
| 6,607,553 B1 | 8/2003 | Healy et al. | 7,131,979 B2 | 11/2006 | DiCarlo et al. |
| 6,612,982 B1 | 9/2003 | Ouchi | 7,160,258 B2 | 1/2007 | Imran et al. |
| 6,616,676 B2 | 9/2003 | Bashiri et al. | 7,171,285 B2 | 1/2007 | Kim et al. |
| 6,623,519 B2 | 9/2003 | Edwin et al. | 7,181,261 B2 | 2/2007 | Silver et al. |
| 6,632,216 B2 | 10/2003 | Houzego et al. | 7,195,641 B2 | 3/2007 | Palmaz et al. |
| 6,638,273 B1 | 10/2003 | Farley et al. | 7,212,110 B1 | 5/2007 | Martin et |
| 6,648,908 B2 | 11/2003 | Dobak, III et al. | 7,214,182 B2 | 5/2007 | Shimizu et al. |
| 6,666,860 B1 | 12/2003 | Takahashi | 7,228,162 B2 | 6/2007 | Ward et al. |
| 6,669,683 B2 | 12/2003 | Santini, Jr. et al. | 7,236,821 B2 | 6/2007 | Cates et al. |
| 6,673,042 B1 | 1/2004 | Samson et al. | 7,245,954 B2 | 7/2007 | Glukhovsky |
| 6,673,363 B2 | 1/2004 | Luo et al. | 7,297,113 B1 | 11/2007 | Russell et al. |
| 6,679,893 B1 | 1/2004 | Tran | 7,341,577 B2 | 3/2008 | Gill |
| 6,709,388 B1 | 3/2004 | Mosse et al. | 7,365,509 B2 | 4/2008 | Park et al. |
| 6,711,423 B2 | 3/2004 | Colvin, Jr. | 7,365,614 B2 | 4/2008 | McCorquodale et al. |
| 6,712,835 B2 | 3/2004 | Mazzocchi et al. | 7,383,071 B1 | 6/2008 | Russell et al. |
| 6,719,684 B2 | 4/2004 | Kim et al. | 7,398,734 B1 | 7/2008 | Jean |
| 6,723,092 B2 | 4/2004 | Brown et al. | 7,451,537 B2 | 11/2008 | Liu et al. |
| 6,733,485 B1 | 5/2004 | Whitehurst et al. | 7,486,967 B2 | 2/2009 | Pan et al. |
| 6,735,474 B1 | 5/2004 | Loeb et al. | 7,572,228 B2 | 8/2009 | Wolinsky et al. |
| 6,735,475 B1 | 5/2004 | Whitehurst et al. | 7,596,403 B2 | 9/2009 | Horn |
| 6,743,211 B1 | 6/2004 | Prausnitz et al. | 7,625,338 B2 | 12/2009 | Gilad et al. |
| 6,754,536 B2 | 6/2004 | Swoyer et al. | 7,684,840 B2 | 3/2010 | Palti |
| 6,755,802 B2 | 6/2004 | Bell | 7,713,196 B2 | 5/2010 | Baker, Jr. |
| 6,755,803 B1 | 6/2004 | Le et al. | 7,736,300 B2 | 6/2010 | Ziegler et al. |
| 6,764,441 B2 | 7/2004 | Chiel et al. | 7,744,542 B2 | 6/2010 | Piaget et al. |
| 6,770,071 B2 | 8/2004 | Woloszko et al. | 7,801,626 B2 | 9/2010 | Moser |
| 6,773,429 B2 | 8/2004 | Sheppard, Jr. et al. | 7,840,271 B2 | 11/2010 | Kieval et al. |
| 6,776,165 B2 | 8/2004 | Jin | 7,857,767 B2 | 12/2010 | Ferren et al. |
| 6,797,522 B1 | 9/2004 | Still et al. | 2001/0029348 A1 | 10/2001 | Willis |
| 6,802,811 B1 | 10/2004 | Slepian | 2001/0051766 A1 | 12/2001 | Gazdzinski |
| 6,816,632 B1 | 11/2004 | Slice | 2002/0026188 A1 | 2/2002 | Balbierz et al. |
| 6,824,508 B2 | 11/2004 | Kim et al. | 2002/0065509 A1* | 5/2002 | Lebel et al. ............... 604/892.1 |
| 6,824,510 B2 | 11/2004 | Kim et al. | 2002/0068080 A1 | 6/2002 | Lerner |
| 6,824,561 B2 | 11/2004 | Soykan et al. | 2002/0090388 A1 | 7/2002 | Humes et al. |
| 6,834,118 B2 | 12/2004 | Kim | 2002/0103417 A1 | 8/2002 | Gazdzinski |
| 6,849,183 B2 | 2/2005 | Gorsuch et al. | 2002/0116029 A1 | 8/2002 | Miller et al. |
| 6,855,115 B2 | 2/2005 | Fonseca et al. | 2002/0116034 A1 | 8/2002 | Miller et al. |
| 6,860,867 B2 | 3/2005 | Seward et al. | 2002/0120263 A1 | 8/2002 | Brown et al. |
| 6,861,001 B2 | 3/2005 | Lee et al. | 2002/0147480 A1 | 10/2002 | Mamayek |
| 6,866,626 B2 | 3/2005 | Long et al. | 2002/0156462 A1* | 10/2002 | Stultz ........................ 604/891.1 |
| 6,869,430 B2 | 3/2005 | Balbierz et al. | 2002/0165592 A1 | 11/2002 | Glukhovsky et al. |
| 6,875,209 B2 | 4/2005 | Zvuloni et al. | 2002/0169436 A1 | 11/2002 | Gurm et al. |
| 6,882,881 B1 | 4/2005 | Lesser et al. | 2002/0171385 A1 | 11/2002 | Kim et al. |
| 6,889,091 B2 | 5/2005 | Hine et al. | 2002/0183721 A1 | 12/2002 | Santini, Jr. et al. |
| 6,890,303 B2 | 5/2005 | Fitz | 2002/0188323 A1 | 12/2002 | Penner et al. |
| 6,898,464 B2 | 5/2005 | Edell et al. | 2002/0193679 A1 | 12/2002 | Malave et al. |
| 6,911,004 B2 | 6/2005 | Kim et al. | 2002/0193874 A1 | 12/2002 | Crowley |
| 6,911,496 B2 | 6/2005 | Rhee et al. | 2002/0198470 A1 | 12/2002 | Imran et al. |
| 6,920,359 B2 | 7/2005 | Meadows et al. | 2002/0198521 A1 | 12/2002 | Maguire |
| 6,921,413 B2 | 7/2005 | Mahadevan-Jansen et al. | 2002/0198604 A1 | 12/2002 | Schulman et al. |
| 6,925,357 B2 | 8/2005 | Wang et al. | 2003/0004403 A1 | 1/2003 | Drinan et al. |
| 6,929,636 B1 | 8/2005 | Von Alten | 2003/0023150 A1 | 1/2003 | Yokoi et al. |
| 6,936,003 B2 | 8/2005 | Iddan | 2003/0024534 A1 | 2/2003 | Silvestri et al. |
| 6,939,290 B2 | 9/2005 | Iddan | 2003/0040704 A1 | 2/2003 | Dorros et al. |
| 6,939,376 B2 | 9/2005 | Shulze et al. | 2003/0060723 A1 | 3/2003 | Joo et al. |
| 6,950,707 B2 | 9/2005 | Whitehurst | 2003/0065250 A1 | 4/2003 | Chiel et al. |
| 6,953,589 B1 | 10/2005 | Trautman et al. | 2003/0065358 A1 | 4/2003 | Frecker et al. |
| 6,958,034 B2 | 10/2005 | Iddan | 2003/0069475 A1 | 4/2003 | Banik et al. |
| 6,959,215 B2 | 10/2005 | Gliner et al. | 2003/0069523 A1 | 4/2003 | Williams et al. |
| 6,960,227 B2 | 11/2005 | Jones et al. | 2003/0093031 A1 | 5/2003 | Long et al. |
| 6,963,792 B1 | 11/2005 | Green | 2003/0151524 A1 | 8/2003 | Clark |
| 6,984,205 B2 | 1/2006 | Gazdzinski | 2003/0152823 A1 | 8/2003 | Heller |
| 6,984,952 B2 | 1/2006 | Peless et al. | 2003/0153866 A1 | 8/2003 | Long et al. |
| 6,991,617 B2 | 1/2006 | Hektner et al. | 2003/0158584 A1 | 8/2003 | Cates et al. |
| 7,003,352 B1 | 2/2006 | Whitehurst | 2003/0163177 A1 | 8/2003 | Eggers et al. |
| 7,013,177 B1 | 3/2006 | Whitehurst et al. | 2003/0167000 A1 | 9/2003 | Mullick et al. |
| 7,020,231 B1 | 3/2006 | Frey et al. | 2003/0191430 A1 | 10/2003 | D'Andrea et al. |
| 7,027,134 B1 | 4/2006 | Garcia-Rubio et al. | 2003/0214579 A1 | 11/2003 | Iddan |

| | | | |
|---|---|---|---|
| 2003/0214580 A1 | 11/2003 | Iddan | |
| 2003/0220556 A1 | 11/2003 | Porat et al. | |
| 2004/0008853 A1 | 1/2004 | Pelrine et al. | |
| 2004/0018508 A1 | 1/2004 | Friedman | |
| 2004/0019374 A1 | 1/2004 | Hojeibane et al. | |
| 2004/0034332 A1 | 2/2004 | Uhland | |
| 2004/0064093 A1 | 4/2004 | Hektner et al. | |
| 2004/0073177 A1 | 4/2004 | Hickle | |
| 2004/0073190 A1 | 4/2004 | Deem et al. | |
| 2004/0092825 A1 | 5/2004 | Madar et al. | |
| 2004/0097805 A1 | 5/2004 | Verard et al. | |
| 2004/0097819 A1 | 5/2004 | Duarte | |
| 2004/0098030 A1 | 5/2004 | Makower et al. | |
| 2004/0111019 A1 | 6/2004 | Long | |
| 2004/0133147 A1 | 7/2004 | Woo | |
| 2004/0138517 A1 | 7/2004 | Osorio et al. | |
| 2004/0147939 A1 | 7/2004 | Rabkin et al. | |
| 2004/0148034 A1 | 7/2004 | Kagan et al. | |
| 2004/0152988 A1 | 8/2004 | Weirich | |
| 2004/0162469 A1 | 8/2004 | Imran | |
| 2004/0162501 A1 | 8/2004 | Imran | |
| 2004/0176664 A1 | 9/2004 | Iddan | |
| 2004/0193010 A1 | 9/2004 | Fujimori et al. | |
| 2004/0199246 A1 | 10/2004 | Chu et al. | |
| 2004/0225325 A1 | 11/2004 | Bonutti | |
| 2004/0225326 A1 | 11/2004 | Weiner et al. | |
| 2004/0260391 A1 | 12/2004 | Santini, Jr. et al. | |
| 2004/0267240 A1 | 12/2004 | Gross et al. | |
| 2005/0004474 A1 | 1/2005 | Iddan | |
| 2005/0004553 A1* | 1/2005 | Douk | 604/523 |
| 2005/0021023 A1 | 1/2005 | Guglielmi et al. | |
| 2005/0027236 A1* | 2/2005 | Douk | 604/40 |
| 2005/0043583 A1 | 2/2005 | Killmann et al. | |
| 2005/0058701 A1 | 3/2005 | Gross et al. | |
| 2005/0062562 A1 | 3/2005 | Ries | |
| 2005/0065592 A1 | 3/2005 | Holzer | |
| 2005/0069925 A1 | 3/2005 | Ford et al. | |
| 2005/0079132 A1 | 4/2005 | Wang et al. | |
| 2005/0107870 A1 | 5/2005 | Wang et al. | |
| 2005/0113460 A1 | 5/2005 | Glick | |
| 2005/0121411 A1 | 6/2005 | Cohen | |
| 2005/0126916 A1 | 6/2005 | Lockard et al. | |
| 2005/0149170 A1 | 7/2005 | Van Tassel et al. | |
| 2005/0151524 A1 | 7/2005 | Sae-Ueng et al. | |
| 2005/0171418 A1 | 8/2005 | Lin | |
| 2005/0171434 A1 | 8/2005 | Madden et al. | |
| 2005/0177223 A1 | 8/2005 | Palmaz | |
| 2005/0182482 A1 | 8/2005 | Wang et al. | |
| 2005/0203613 A1 | 9/2005 | Arney et al. | |
| 2005/0215911 A1 | 9/2005 | Alfano et al. | |
| 2005/0216074 A1 | 9/2005 | Sahatjian et al. | |
| 2005/0221529 A1 | 10/2005 | Bang et al. | |
| 2005/0228259 A1 | 10/2005 | Glukhovsky et al. | |
| 2005/0234393 A1 | 10/2005 | Wood, Jr. | |
| 2005/0234440 A1 | 10/2005 | Wood, Jr. | |
| 2005/0238689 A1 | 10/2005 | Carpenter et al. | |
| 2005/0272806 A1 | 12/2005 | Falotico et al. | |
| 2005/0272974 A1 | 12/2005 | Iddan | |
| 2005/0277839 A1 | 12/2005 | Alderman et al. | |
| 2005/0278020 A1 | 12/2005 | Wang et al. | |
| 2006/0004395 A1 | 1/2006 | Chiel et al. | |
| 2006/0009810 A1 | 1/2006 | Mann et al. | |
| 2006/0015146 A1 | 1/2006 | Girouard et al. | |
| 2006/0037617 A1 | 2/2006 | Walke et al. | |
| 2006/0042631 A1 | 3/2006 | Martin et al. | |
| 2006/0074479 A1 | 4/2006 | Bailey et al. | |
| 2006/0119304 A1 | 6/2006 | Farritor et al. | |
| 2006/0152309 A1 | 7/2006 | Mintchev et al. | |
| 2006/0167339 A1 | 7/2006 | Gilad et al. | |
| 2006/0169294 A1 | 8/2006 | Kaler et al. | |
| 2006/0235275 A1 | 10/2006 | Rabinovitz et al. | |
| 2006/0252987 A1 | 11/2006 | Hasegawa et al. | |
| 2007/0010868 A1 | 1/2007 | Ferren et al. | |
| 2007/0066929 A1 | 3/2007 | Ferren et al. | |
| 2007/0088334 A1 | 4/2007 | Hillis et al. | |
| 2007/0156211 A1 | 7/2007 | Ferren et al. | |
| 2007/0225634 A1 | 9/2007 | Ferren et al. | |
| 2008/0063703 A1 | 3/2008 | Gross et al. | |
| 2008/0066929 A1 | 3/2008 | Costa et al. | |
| 2008/0121054 A1 | 5/2008 | Goldenberg et al. | |
| 2008/0241847 A1 | 10/2008 | Hoon et al. | |
| 2008/0243056 A1 | 10/2008 | Hillis et al. | |
| 2008/0266106 A1 | 10/2008 | Lim et al. | |
| 2009/0062646 A1 | 3/2009 | Creighton, IV et al. | |
| 2009/0069821 A1 | 3/2009 | Farritor et al. | |
| 2009/0082652 A1 | 3/2009 | Koh et al. | |
| 2009/0182388 A1 | 7/2009 | Von Arx et al. | |

FOREIGN PATENT DOCUMENTS

| | | |
|---|---|---|
| EP | 1 245 201 A1 | 10/2002 |
| EP | 1 618 831 A2 | 1/2006 |
| EP | 2 163 206 A1 | 3/2010 |
| JP | 2001-506871 | 3/1998 |
| JP | 2002-153569 | 5/2002 |
| JP | 2005-74229 | 3/2005 |
| WO | WO 96/39999 | 12/1996 |
| WO | WO 98/09582 | 3/1998 |
| WO | WO 98/14243 | 4/1998 |
| WO | WO 99/20335 | 4/1999 |
| WO | WO 99/44665 | 9/1999 |
| WO | WO 00/69515 | 11/2000 |
| WO | WO 01/08548 A1 | 2/2001 |
| WO | WO 01/24731 A1 | 4/2001 |
| WO | WO 03/072157 A1 | 9/2003 |
| WO | WO 03/090618 A2 | 11/2003 |
| WO | WO 03/106966 A2 | 12/2003 |
| WO | WO 2004/028335 A2 | 4/2004 |
| WO | WO 2004/058041 A2 | 7/2004 |
| WO | WO 2004/086958 A1 | 10/2004 |
| WO | WO 2005/082248 A1 | 9/2005 |

OTHER PUBLICATIONS

U.S. Appl. No. 11/645,358, Ferren et al.
U.S. Appl. No. 11/645,357, Ferren et al.
U.S. Appl. No. 11/485,619, Hillis et al.
U.S. Appl. No. 11/478,368, Ferren et al.
U.S. Appl. No. 11/417,898, Hillis et al.
U.S. Appl. No. 11/403,230, Ferren et al.
U.S. Appl. No. 10/949,186, Hillis et al.
UK Intellectual Property Office Examination Report Under Section 18(3); App. No. GB0706802.6; bearing a date of Dec. 1, 2008; pp. 1-2.
U.S. Appl. No. 12/075,480, Hillis et al.
U.S. Appl. No. 11/891,573, Wood, Jr., Lowell L.
U.S. Appl. No. 11/891,371, Wood, Jr., Lowell L.
U.S. Appl. No. 11/891,356, Wood, Jr., Lowell L.
U.S. Appl. No. 11/891,355, Wood, Jr., Lowell L.
U.S. Appl. No. 11/891,334, Wood, Jr., Lowell L.
U.S. Appl. No. 11/891,333, Wood, Jr., Lowell L.
U.S. Appl. No. 11/726,031. Ferren et al.
U.S. Appl. No. 11/726,025, Ferren et al.
U.S. Appl. No. 11/725,982, Ferren et al.
PCT International Search Report; International App. No. PCT/US05/13349; Apr. 28, 2008; pp. 1-2.
PCT International Search Report; International App. No. PCT/US2007/008993; Sep. 29, 2008; pp. 1-3.
PCT International Search Report; International App. No. PCT/US07/10819; Aug. 27, 2008; pp. 1-3.
PCT International Search Report; International App. No. PCT/US07/10824; Aug. 21, 2008; pp. 1-3.
PCT International Search Report; International App. No. PCT/US07/10942; Aug. 15, 2008; pp. 1-3.
PCT International Search Report; International App. No. PCT/US07/10936; Jul. 24, 2008; pp. 1-3.
PCT International Search Report; International App. No. PCT/US07/10857; Jul. 21, 2008; pp. 1-2.
PCT International Search Report; International App. No. PCT/US 07/10969, Nov. 10, 2008; pp. 1-2.
UK Intellectual Property Office Examination Report Under Section 18(3), App. No. GB0821523.8; Jul. 2, 2009; pp. 1-2.
UK Intellectual Property Office Examination Report Under Section 18(3); App. No. GB0821519.6; Nov. 12, 2009; pp. 1-4.

UK Intellectual Property Office Examination Report Under Section 18(3); App. No. GB0821526.1; Nov. 11, 2009; pp. 1-5.
UK Examination Report Under Section 18(3); App. No. GB0821524.6; bearing a date of May 6, 2010; pp. 1-3.
UK Intellectual Property Office Examination Report Under Section 18(3); App. No. GB0706802.6; Nov. 23, 2009; pp. 1-2.
UK Intellectual Property Office Examination Report under Section 18(3); App. No. GB0821521.2; Jan. 12, 2011; pp. 1-4.
U.S. Appl. No. 12/928,455, Wood, Jr., Lowell L.
U.S. Appl. No. 12/930,916, Wood, Jr., Lowell L.
"001_08 Comparison of Capsule Cameras: M2A (Given Imaging) vs. NORIKA3 (RF System lab)" RF System lab; bearing dates of 2001-2004; pp. 1-2; located at http://www.rfnorika.com/eng/system/sys_008.html; printed on May 4, 2006.
"A Hydrogel-based CO2 sensor"; BIOS—The lab on a chip group; bearing a date of Aug. 29, 2005; pp. 1-2; located at: http://bios.ewi.utwente.nl/research/analysissystemssenors/ahydrogelbased.doc/index.html; printed on Apr. 25, 2006; University of Twente; the Netherlands.
Agarwal, Abhishek K.; Atencia, Javier; Beebe, David J.; Jiang, Hongrui; "Magnetically-driven temperature-controlled microfluidic actuators"; pp. 1-5; located at: http://www.unl.im.dendai.ac.jp/INSS2004/INSS2004_papers/OralPresentations/C2.pdf.
"Agile new plastics change shape with heat"; MIT News Office; Nov. 20, 2006; pp. 1-4; Massachusetts Institute of Technology; printed on Nov. 22, 2006; located at http://web.mit.edu/newsoffice/2006/triple-shape.html.
"Agile new plastics change shape with heat"; MIT Tech Talk; Nov. 22, 2006; p. 5 (1 page).
Ananthaswamy, Anil; "First robot moved by muscle power"; bearing a date of Feb. 27, 2004; pp. 1-3; New Scientist; located at http://www.newscientist.com/article.ns?id=dn4714; printed on Sep. 12, 2006.
Asari, Vijayan K.; Kumar, Sanjiv; Kassim, Irwan M.; "A Fully Autonomous Microrobotic Endoscopy System"; Journal of Intelligent and Robotic Systems; bearing a date of 2000; pp. 325-341; vol. 28; Kluwer Academic Publishers.
Behkam, Bahareh; Sitti, Metin; "Towards Hybrid Swimming Microrobots: Bacteria Assisted Propulsion of Polystyrene Beads"; Proceedings of the 28$^{th}$ IEEE EMBS Annual International Conference; bearing dates of Aug. 30, 2006-Sep. 3, 2006 and 2006; pp. 2421-2424; IEEE.
Berlinger, Norman T.; "Robotic Surgery—Squeezing into Tight Places"; New England Journal of Medicine; bearing dates of May 17, 2006, May 18, 2006, and 2006; pp. 2099-2101; Massachusetts Medical Society; located at www.nejm.org.
Bezrouk, A.; Hanuš, J.; Záhora, J.; "Temperature Characteristics of Nitinol Spiral Stents"; Scripta Medica (BRNO); bearing dates of Aug. 2005, Oct. 2005; pp. 219-226; vol. 78, No. 4.
Bialek, William; Rieke, Fred; De Ruyter Van Steveninck, Rob R.; Warland, David; "Reading a Neural Code"; Science; bearing a date of Jun. 28, 1991; pp. 1854-1857; vol. 252.
Bucher, Volker; Graf, Michael; Stelzle, Martin; Nisch, Wilfried; "Low-Impedance Thin-Film Polycrystalline Silicon Microelectrodes for Extracellular Stimulation and Recording"; Biosensors and Bioelectronics; bearing a date of 1999; pp. 639-649; vol. 14; Elsevier Science S.A.; located at: www.elsevier.com/locate/bios.
Butson, Christopher R.; McIntyre, Cameron C.; "Role of Electrode Design on the Volume of Tissue Activated During Deep Brain Stimulation"; Journal of Neural Engineering; bearing a date of 2006; vol. 3; pp. 1-8; IOP Publishing Ltd.
Chang, Suk Tai; Paunov, Vesselin N.; Petsev, Dimiter N.; Velev, Orlin D.; "Articles: Remotely Powered Self-Propelling Particles and Micropumps Based on Miniature Diodes"; Nature Materials; bearing a date of 2007; pp. 1-6; Nature Publishing Group; located at: www.nature.com/naturematerials.
Chen, Haitao; Ebner, Armin D.; Ritter, James A.; Kaminski, Michael D.; Rosengart, Axel J.; "Sequestration of Blood-Borne Magnetic Drug Carrier Particles Using Magnetizable Intravascular Stents"; Collaborative Investigators for Applied Nanotechnology in Medicine; pp. 1; Chicago, Illinois, May 2005.
Chen, Ting; Barton, Scott Calabrese; Binyamin, Gary; Gao, Zhiqiang; Zhang, Yongchao; Kim, Hyug-Han; Heller, Adam; "A Miniature Biofuel Cell"; Journal of the American Chemical Society; Aug. 11, 2001; pp. 8630-8631; vol. 123; 2001 American Chemical Society.
Christensen, Bill; "Musclebot: Microrobot with a Heart"; Technovelgy.com; pp. 1-2; bearing a date of Feb. 27, 2004; located at http://www.technovelgy.com/ct/Science-Fiction-News.asp?NewsNum=46; printed on Sep. 12, 2006.
Christensen, Bill; "Propulsion System for 'Fantastic Voyage' Robot"; Technovelgy.com; pp. 1-4; Technovelgy.com; located http://www.technovelgy.com/ct/Science-Fiction-News.asp?NewsNum=811; printed on Jan. 4, 2007.
Costamagna; Guido M.D.; "PillCam™ SB Capsule Endoscopy"; Given Imaging.com; bearing dates of 2001-2006; pp. 1-4; located at http://www.givenimaging.com/Cultures/en-US/Given/English/Products/CapsuleEndoscopy/; printed on May 4, 2006.
Cui, Xinyan; Hetke, Jamille F.; Wiler, James A.; Anderson, David J.; Martin, David C.; "Electrochemical Deposition and Characterization of Conducting Polymer Polypyrrole/PPS on Multichannel Neural Probes"; Sensors and Actuators A Physical; bearing a date of 2001; pp. 8-18; vol. 93; Elsevier Science B.V.; located at: www.elsevier.com/locate/sna.
Dario, P.; Carrozza, M.C.; Lencioni, L.; Magnani, B.; D'Attanasio, S.; "A Micro Robotic System for Colonoscopy"; Proceedings of the 1997 IEEE International Conference on Robotics and Automation; bearing dates of Apr. 1997 and 1997; pp. 1567-1572; IEEE.
Dillier, Norbert; Lai, Wai Kong; Almqvist, Bengt; Frohne, Carolin; Müller-Deile, Joachim; Stecker, Matthias; Von Wallenberg, Ernst; "Measurement of the Electrically Evoked Compound Action Potential Via a Neural Response Telemetry System"; Annals of Otology Rhinology and Laryngology; bearing a date of May 2002; pp. 407-414; vol. 111, No. 5; Annals Publishing Company.
Dongxiang, Chi; Guozheng, Yan; "An earthworm based miniature robot for intestinal inspection"; Proceedings of SPIE; bearing dates of Nov. 7, 2001-Nov. 9, 2001; pp. 396-400; vol. 4601; SPIE.
Donoghue, John P.; "Review: Connecting Cortex to Machines: Recent Advances in Brain Interfaces"; Nature Neuroscience Supplement; bearing a date on Nov. 2002; pp. 1085-1088; vol. 5; Nature Publishing Group; located at: http://www.nature.com/natureneuroscience.
Fang, Zi-Ping; Mortimer, J. Thomas; "Selective Activation of Small Motor Axons by Quasitrapezoidal Current Pulses"; IEEE Transactions on Biomedical Engineering; bearing a date of Feb. 1991; pp. 168-174; vol. 38, No. 2; IEEE.
Fiaccabrino, G.C.; Tang, X.-M.; Skinner, N.; De Rooij, N.F.; Koudelka-Hep, M.; "Electrochemical Characterization of Thin-Film Carbon Interdigitated Electrode Arrays"; Analytica Chimica Acta; bearing a date of 1996; pp. 155-160; vol. 326; Elsevier Science B.V.
Freitas Jr., Robert A.; "8.2.1.2 Arteriocenous Microcirculation"; "9.4.3.5 Legged Ambulation"; "9.4.3.6 Tank-Tread Rolling"; "9.4.3.7 Amoeboid Locomotion"; "9.4.3.8 Inchworm Locomotion"; "Nanomedicine vol. I: Basic Capabilities"; bearing a date of 1999; pp. 211-214, pp. 316-318; Landes Bioscience; Georgetown, Texas, USA.
Gitter, Alfred H.; Fromm, Michael; Schulzke, Jörg-Dieter; "Impedance Analysis for the Determination of Epithelial and Subepithelial Resistance in Intestinal Tissues"; Journal of Biochemical and Biophysical Methods, bearing a date of 1998; pp. 35-46; vol. 37; Elsevier Science B.V.
Goda, Yukiko; Colicos, Michael A.; "Protocol: Photoconductive Stimulation of Neurons Cultured on Silicon Wafers"; Nature Protocols; bearing a date of 2006; pp. 461-467; vol. 1, No. 1; Nature Publishing Group; located at: http://www.nature.com/natureprotocols.
Gozani, Shai N.; Miller, John P.; "Optimal Discrimination and Classification of Neuronal Action Potential Waveforms from Multiunit, Multichannel Recordings Using Software-Based Linear Filters"; IEEE Transactions on Biomedical Engineering; bearing a date of Apr. 1994; pp. 358-372; vol. 41, No. 4; IEEE.
Gray, Charles M.; Maldonado, Pedro E.; Wilson, Mathew; McNaughton, Bruce; "Tetrodes Markedly Improve the Reliability and Yield of Multiple Single-Unit Isolation from Multi-Unit Recordings in Cat Striate Cortex"; Journal of Neuroscience Methods; bearing a date of 1995; pp. 43-54; vol. 63; Elsevier Science B.V.

Hagleitner, C.; Hierlemann, A.; Lange, D.; Kummer, A.; Kerness, N.; Brand, O.; Baltes, H.; "Smart single-chip gas sensor microsystem"; Nature; Nov. 15, 2001; pp. 293-296; vol. 414; Macmillan Magazines Ltd.; www.nature.com.

Hanna, Darrin M.; Oakley, Barbara A.; Stryker, Gabrielle A.; "Using a System-on-Chip Implantable Device to Filter Circulating Infected Cells in Blood or Lymph"; IEEE Transactions on Biomedical Engineering; bearing dates of Jan. 25, 2003, Mar. 2003; pp. 6-13; vol. 2, No. 1; IEEE.

Hodgkin, A.L.; Huxley, A.F.; "A Quantitative Description of Membrane Current and its Application to Conduction and Excitation in Nerve"; Journal of Physiology; bearing a date of 1952; pp. 500-544; vol. 117.

Høeg, H.D.; Slatkin, A.B.; Burdick, J.W.; Grundfest, Dr. Warren S.; "Biomechanical Modeling of the Small Intestine as Required for the Design and Operation of a Robotic Endoscope"; Proceedings ICRA '00 IEEE International Conference on Robotics and Automation; Apr. 24, 2000-Apr. 28, 2000; pp. 1-8; vol. 2.

Hofmann, U.G.; Folkers, A.; Mösch, F.; Höhl, D.; Kindlundh, M.; Norlin, P.; "A 64(128)-Channel Multisite Neuronal Recording System"; bearing a date of 2002; pp. 1-4.

Ikeuchi, K.; Yoshinaka, K.; Hashimoto, S.; Tomita, N.; "Locomotion of Medical Micro Robot with Spiral Ribs Using Mucus"; Seventh International Symposium on Micro Machine and Human Science; bearing a date of 1996; pp. 217-222; IEEE.

Inmann, Andreas; Haugland, Morten; Haase, Jens; Biering-Sørensen, Fin; Sinkjaer, Thomas; "NeuroReport: Signals from Skin Mechanoreceptors used in Control of a Hand Grasp Neuroprosthesis"; Motor Systems; bearing a date of Sep. 17, 2001; pp. 2817-2819; vol. 12, No. 13; Lippincott Williams & Wilkins.

Janders, M.; Egert, U.; Stelze, M.; Nisch, W.; "Novel Thin Film Titanium Nitride Micro-Electrodes with Excellent Charge Transfer Capability for Cell Stimulation and Sensing Applications"; IEEE Engineering in Medicine and Biology Society; bearing a date of 1996; pp. 245-247; IEEE.

"Japanese Researchers Unveil Medical Mini Robot"; Yahoo! News; bearing a date of Mar. 8, 2007; pp. 1-2; Yahoo! Inc.; located at: http://news.yahoo.com/s/afp/20070308/hl_afp/afplifestyleshealthscience; printed on Mar. 8, 2007.

Ji, Jin; Najafi, Khalil, Wise, Kensall D.; "A Low-Noise Demultiplexing System for Active Multichannel Microelectrode Arrays"; IEEE Transactions of Biomedical Engineering; bearing a date of Jan. 1991; pp. 77-81; vol. 38, No. 1; IEEE.

Kassim, Irwan; Phee, Louis; NG, Wan S.; Gong, Feng; Dario, Paolo; Mosse, Charles A.; "Locomotion Techniques for Robotic Colonoscopy"; IEEE Engineering in Medicine and Biology Magazine; bearing dates of May/Jun. 2006 and 2006; pp. 49-56; IEEE.

Kennedy, P.R.; Bakay, R.A.E.; Moore, M.M.; Adams, K.; Goldwaithe, J.; "Direct Control of a Computer from the Human Central Nervous System"; IEEE Transactions on Rehabilitation Engineering; bearing a date of Jun. 2000; pp. 198-202; vol. 8, No. 2; IEEE.

Kobetic, Rudi; Triolo, Ronald J.; Uhlir, James P.; Bieri, Carole; Wibowo, Michael; Polando, Gordie; Marsolais, E. Byron; Davis Jr., John A.; Ferguson, Kathleen A.; Sharma, Mukut; "Implanted Functional Electrical Stimulation System for Mobility in Paraplegia: A Follow-Up Case Report"; IEEE Transactions on Rehabilitation Engineering; bearing a date of Dec. 1999; pp. 390-398; vol. 7, No. 4; IEEE.

Krueger, Curtis; "New light on blood testing"; Oct. 20, 2006; pp. 1-2; St. Petersburg Times; printed on Oct. 24, 2006; located at http://www.sptimes.com/2006/10/20news_pf/Tampabay/New_light_on_blood_te.shtml.

Langer, Robert; Peppas, Nicholas A.; Advances in Biomaterials, Drug Delivery, and Bionanotechnology;; AIChE Journa—Bioengineering, Food, and Natural Products; Dec. 2003; pp. 2990-3006; vol. 49, No. 12.

Loeb, G.E.; Peck, R.A.; Martyniuk, J.; "Toward the Ultimate Metal Microelectrode"; Journal of Neuroscience Methods; bearing a date of 1995; pp. 175-183; vol. 63; Elsevier Science B.V.

Loeb, Gerald E.; Peck, Raymond A.; Moore, William H.; Hood, Kevin; "BION System for Distributed Neural Prosthetic Interfaces"; Medical Engineering and Physics; bearing a date of 2001; pp. 9-18; vol. 23; Elsevier Science Ltd.; located at: www.elsevier.com/locate/medengphy.

Lu, Zhao; Martel, Sylvain; "Preliminary Investigation of Bio-carriers Using Magnetotactic Bacteria"; Proceedings of the 28th IEEE EMBS Annual International Conference; bearing dates of Aug. 30, 2006-Sep. 3, 2006 and 2006; pp. 3415-3418; IEEE.

Mangan, Elizabeth V.; Kingsley, Dan A.; Quinn, Roger D.; Chiel, Hillel J.; "Development of a Peristaltic Endoscope"; IEEE International Conference on Robotics & Automation 2002; pp. 1-6; located at http://biorobots.cwru.edu/publications/ICRA02_Mangan_Endoscope.pdf.

Marks, William B.; Loeb, Gerald E.; "Action Currents, Internodal Potentials, and Extracellular Records of Myelinated Mammalian Nerve Fibers Derived from Node Potentials"; Biophysical Journal; 1976; pp. 655-668; vol. 16.

Martel, Sylvain; "Fundamentals of high-speed piezo-actuated three-legged motion for miniature robots designed for nanometer-scale operations"; pp. 1-8, Jul. 2005.

Martel, Sylvain; "Towards MRI-Controlled Ferromagnetic and MC-1 Magnetotactic Bacterial Carriers for Targeted Therapies in Arteriolocapillar Networks Stimulated by Tumoral Angiogenesis"; Proceedings of the 28th IEEE EMBS Annual International Conference; bearing dates of Aug. 30, 2006-Sep. 3, 2006 and 2006; pp. 3399-3402; IEEE.

Martel, Sylvain; Mathieu, Jean-Baptiste; Felfoul, Ouajdi; Chanu, Arnaud; Aboussouan, Eric; Tamaz, Samer; Pouponneau, Pierre; "Automatic Navigation of an Untethered Device in the Artery of a Living Animal using a Conventional Clinical Magnetic Resonance Imaging System"; Applied Physics Letters; 2007; pp. 114105-1-114105-3; vol. 90, No. 114105; American Institute of Physics.

Mathieu, J-B.; Martel, S.; Yahia, L'H.; Soulez, G.; Beaudoin, G.; "MRI Systems as a Mean of Propulsion for a Microdevice in Blood Vessels"; bearing a date of 2003; pp. 3419-3422; IEEE.

Matsui, Takemi; Matsumura, Kouji; Hagisawa, Kousuke; Ishihara, Masayuki; Ishizuka, Toshiaki; Suzuki, Minoru; Kurita, Akira; Kikuchi, Makoto; "A Novel Ferromagnetic Thermo-Stent for Plaque Stabilization That Self-Regulates the Temperature"; IEEE Transactions on Biomedical Engineering; bearing dates of Jun. 2002 and 2002; pp. 621-623; vol. 49, No. 6; IEEE.

McNeal, Donald R.; "Analysis of a Model for Excitation of Myelinated Nerve"; IEEE Transactions on Biomedical Engineering; bearing a date of Jul. 1976; pp. 329-337; vol. BME-23, No. 4.

Meier, P.; Oberthür, S.; Lang, M.; "Development of a compliant device for minimally invasive surgery"; Proceedings of the 28th IEEE EMBS Annual International Conference; bearing dates of Aug. 30, 2006-Sep. 3, 2006 and 2006; pp. 331-334; IEEE.

"MEMS at the cutting edge®, Patent Pending"; VERIMETRA; pp. 1-2; located at http://www.verimetra.com/flow.htm; printed on May 4, 2006.

Menciassi, A.; Park, Jong H.; Lee, S.; Gorini, S.; Dario, P.; Park, Jong-Oh; "Robotic Solutions and Mechanisms for a Semi-Autonomous Endoscope"; Proceedings of the 2002 IEEE/RSJ International Conference on Intelligent Robots and Systems; bearing a date of 2002; pp. 1379-1384; IEEE.

Mohseni, Kamran; "Biomimetic & Bio-Inspired Aerial and Underwater Vehicles"; bearing a date of Sep. 23, 2006; pp. 1-10; printed on Jan. 4, 2007; located at http://enstrophy.colorado.edu/~mohseni/MicroVehicles1.html#UUV1#UUV1.

Mosse, Charles; Mills, Tim; Appleyard, Mark; Swain, Paul; "Electrostimulation to move endoscopes in the small bowel"; Proceedings of SPIE; bearing a date of 2001; pp. 24-28; vol. 4158.

Murthy, S. Narasimha; Hiremath, Shobha Rani R.; "Physical and Chemical Permeation Enhancers in Transdermal Delivery of Terbutaline Sulphate"; AAPS PharmSciTech; bearing a date of 2001; pp. 1-5; vol. 2001, 2(1); Technical Note 1; located at http://www.pharmscitech.com/.

Nakayama, Yasuhide; Ji-Youn, Kim; Nishi, Shogo; Ueno, Hikaru; Matsuda, Takehisa; "Development of high-performance stent: gelatinous photogel-coated stent that permits drug delivery and gene transfer"; J Biomed Mater Res; bearing dates of Nov. 13, 2000, Apr. 23, 2001, May 10, 2001 and 2001; pp. 559-566; vol. 57; John Wiley & Sons, Inc.

Naqvi, Nasir H.; Rudrauf, David; Damasio, Hanna; Bechara, Antoine; "Damage to the Insula Disrupts Addiction to Cigarette Smoking"; Science; bearing a date of Jan. 26, 2007; pp. 531-534; vol. 315, No. 531; located at: www.sciencemag.org; printed on Jan. 25, 2007.

Neto, A.M. Figueiredo; Godinho, M.H.; Toth-Katona, T.; Palffy-Muhoray, P.; "Optical, Magnetic and Dielectric Properties of Non-Liquid Crystalline Elastomers Doped with Magnetic Colloids"; Brazilian Journal of Physics; Bearing a date of Mar. 2005; pp. 184-189; vol. 35, No. 1.

"New Medical Device Combines Wireless and MEMS Technology"; Georgia Institute of Technology; pp. 1-4; PhysOrg.com; located at: http://www.physorg.com/printnews.php?newsid=10533; printed on Feb. 20, 2006.

Nieuwenhuizen-Berkovits, P.; "lubrelastic medical appliances"; Lubrelastic Medical Appliances; pp. 1-4; located at: http://www.xs4all.nl/~plien070/caeng.html; printed on Feb. 20, 2006.

Nyitrai, Zsolt; Illyefalvi-Vitéz, Zsolt; Pinkola, János; "Preparing Stents with Masking & Etching Technology"; 26$^{th}$ International Spring Seminar on Electronics Technology; bearing dates of May 8, 2003-May 11, 2003 and 2003; pp. 321-324; IEEE.

Olsson III, R.H.; Gulari, M.N.; Wise, K.D.; "Poster 114: Silicon Neural Recording Arrays with On-Chip Electronics for In-Vivo Data Acquisition"; Microtechnologies in Medicine and Biology; bearing dates of May 2, 2002-May 4, 2002; pp. 237-240; IEEE.

Oweiss, Karim G.; Anderson, David J.; "A New Technique for Blind Source Separation Using Subband Subspace Analysis in Correlated Multichannel Signal Environments"; bearing a date of 2001; pp. 2813-2816; IEEE.

Patronik, N.A.; Ota, T.; Zenati, M.A.; Riviere, C.N.; "Improved Traction for a Mobile Robot Traveling on the Heart"; Proceedings of the 28$^{th}$ IEEE EMBS Annual International Conference; bearing dates of Aug. 30, 2006-Sep. 3, 2006 and 2006; pp. 339-342; IEEE.

PCT International Search Report App. No. PCT/US05/33475; dated Sep. 5, 2006; pp. 1-2.

Peckham, P. Hunter; Knutson, Jayme S.; "Functional Electrical Stimulation for Neuromuscular Applications"; Annual Review Biomedical Engineering; bearing a date of 2005; pp. 327-360; vol. 7; Annual Reviews.

Rattay, F.; "The Basic Mechanism for the Electrical Stimulation of the Nervous System"; Neuroscience; 1999; pp. 335-346; vol. 98. No. 2; Elsevier Science Ltd; printed on Mar. 15, 2007.

Rattay, Frank, Aberham, Matthias; "Modeling Axon Membranes from Functional Electrical Stimulation"; IEEE Transactions on Biomedical Engineering; bearing a date of Dec. 1993; pp. 1201-1209; vol. 40, No. 12; IEEE.

Rattay, Frank; "Analysis of Models for Extracellular Fiber Stimulation"; IEEE Transactions on Biomedical Engineering; bearing a date of Jul. 1989; pp. 676-682; vol. 36, No. 7; IEEE.

"Remote-Control Electrostimulation Capsule"; Popular Science; bearing dates of 2002 and 2003; pp. 1-2; located at http://www.popsci.com/popsci/brown/2003/article/0,18881,537028.00.html; printed on May 4, 2006.

"Researchers: Squid-Inspired Vortex Generators Could Mean Better Propulsion for Unmanned Underwater Vehicles"; UnderwaterTimes.com; Dec. 12, 2006; pp. 1-2; UnderwaterTimes.com; printed on Jan. 4, 2007; located at http://www.underwatertimes.com/print.php?article_id=51030782641.

Rice, Mike; "Implantable Neurostimulation Device Market Poised for Explosive Growth"; Future Fab International; Jan. 7, 2006; pp. 1-4; printed on Oct. 6, 2006; located at http://www.future-fab.com/documents.asp?d_ID=3725.

Rice, Mike; "New Products, Emphasis on Miniaturization Driving Medical Device Innovation"; bearing a date Aug. 23, 2006; pp. 1-3; Advantage Business Media; located at http://www.mdtmag.com/scripts/ShowPR.asp?PUBCODE=046&ACCT=0006109&ISSUE=0603&RELTYPE=PR&PRODCODE=0790&PRODLETT=A; printed on Aug. 23, 2006.

Riedmüller, J.; Bolz, A.; Rebling, H.; Schaldach, M.; "Improvement of Stimulation and Sensing Performance of Bipolar Pacemaker Leads"; IEEE Eng. Med. Biol. Soc.; 1992; pp. 2364-2365; IEEE.

Robinson, David A.; "The Electrical Properties of Metal Microelectrodes"; Proceedings of the IEEE; bearing a date of Jun. 1968; pp. 1065-1071; vol. 56, No. 6.

Rousche, Patrick J.; Pellinen, David S.; Pivin, David P.; Williams, Justin C.; Vetter, Rio J.; Kipke, Daryl R.; "Flexible Polyimide-Based Intracortical Electrode Arrays with Bioactive Capability"; IEEE Transactions on Biomedical Engineering; bearing a date Mar. 2001; pp. 361-371; vol. 48, No. 3; IEEE.

Rutten, Wim; Mouveroux, Jean-Marie; Buitenweg, Jan; Heida, Ciska; Ruardij, Teun; Marani, Enrico; Lakke, Egbert; "Neuroelectronic Interfacing with Cultured Multielectrode Arrays Toward a Cultured Probe"; Proceedings of the IEEE; bearing a date of Jul. 2001; pp. 1013-1029; vol. 89, No. 7; IEEE.

Saltzman, John R.; "Endoscopic Advances—A View Toward the Future"; bearing dates of May 4, 2006, May 17, 2005, and 2005; pp. 1-4; Medscape; located at http://www.medscape.com/viewarticle/505100; printed on May 4, 2006.

Schmidt, W.; Behrens, P.; Behrend, D.; Schmitz, K.-P.; Andresen, R.; "Experimental Study of Peripheral, Balloon-expandable Stent Systems"; Progress in Biomedical Research; bearing a date of May 2001; pp. 246-255.

Schoonhoven, R.; Stegeman, D.F.; "Models and Analysis of Compound Nerve Action Potentials"; Critical Reviews in Biomedical Engineering; bearing a date of 1991; pp. 47-111; vol. 19, No. 1; CRC Press, Inc.

Senel, Sevda; Hincal, A. Atilla; "Drug permeation enhancement via buccal route: possibilities and limitations"; Journal of Controlled Release; bearing a date of 2001; pp. 133-144; vol. 72 (2001); Elsevier; located at www.elsevier.com/locate/jconrel.

Serruya, Mijail D.; Hatsopoulos, Nicholas G.; Paninski, Liam; Fellows, Matthew R.; Donoghue, John P.; "Brief Communications: Instant Neural Control of a Movement Signal"; Nature; bearing a date of Mar. 14, 2002; pp. 141-142; vol. 416; Macmillan Magazines Ltd; located at: www.nature.com.

Serruys, Patrick W.; Kutryk, Michael J.B.; Ong, Andrew T.L.; "Coronary-Artery Stents"; The New England Journal of Medicine; bearing dates of Feb. 2, 2006 and Feb. 15, 2006; pp. 483-495; vol. 354;5; Massachusetts Medical Society.

Shabalovskaya, Svetlana, A.; "Surface, corrosion and biocompatibility aspects of Nitinol as an implant material"; Bio-Medical Materials and Engineering; bearing dates of Apr. 4, 2001, and 2002; pp. 69-109; vol. 12; IOS Press.

Shahinpoor, Mohsen; Kim, Kwang J.; Ionic polymer-metal composites: IV. Industrial and medical applications; Smart Materials and Structures; 2005; pp. 197-214; vol. 14; Institute of Physics Publishing.

Smith, Michael; "PAS: Nasal Spray Flu Vaccine Seems Safe and Effective in Young"; May 2, 2006; pp. 1-2; MedPage Today, LLC; bearing dates of 2004-2006; printed on May 4, 2006; located at http://www.medpagetoday.com/tbprint.cfm?tbid=3213.

Snoek, GJ; Ijzerman, MJ; In 'T Groen, Facg; Stoffers, TS; Zilvold, G; "Use of the NESS Handmaster to Restore Handfunction in Tetraplegia: Clinical Experiences in Ten Patients"; Spinal Cord; bearing a date of 2000; pp. 244-249; vol. 38; International Medical Society of Paraplegia.

Snow, E.S.; Perkins, F.K.; Houser, E.J.; Badescu, S.C.; Reinecke, T. L.; "Chemical Detection with a Single-Walled Carbon Nanotube Capacitor"; Science; Mar. 25, 2005; pp. 1942-1945; vol. 307; www.sciencemag.org.

Stoeckel, Dieter; Pelton, Alan; Duerig, Tom; "Self-expanding nitinol stents: material and design considerations"; European Radiology; bearing dates of Jan. 28, 2003, May 22, 2003, Jul. 1, 2003, Sep. 3, 2003, Feb. 2004 and 2004; pp. 292-301(1-2); vol. 14, No. 2; Springer-Verlag GmbH-SpringerLink—Article; located at: http://www.springerlink.com/(1begg455gtgjfseqqptyb43m)/app/home/contribution.asp?referrer=parent&backto=issue,17,26;journal,27,147;browsepublicationsresults,444,1551; printed on Feb. 22, 2006.

Strauss, Bradley H., M.D., Ph.D.; Li, Chris, M.D.; Whittingham, Heather A., M.Sc; Tio, Fermin O., M.D.; Kutryk, Michael J.B., M.D., Ph.D.; Janicki, Christian, Ph.D.; Sparkes, John, D., M.Sc.; Turnlund, Todd, B.Sc.; Sweet, William L., M.D.; "Late Effects of Low-Energy Gamma-Emitting Stents in a Rabbit ILIAC Artery Model"; Int. J.

Radiation Oncology Biol. Phys.; bearing dates of Oct. 23, 2001, May 13, 2002 and May 15, 2002 and 2002; pp. 551-561; vol. 54, No. 2; Elsevier Science Inc.

Struijk, Johannes Jan; "The Extracellular Potential of a Myelinated Nerve Fiber in an Unbounded Medium and in Nerve Cuff Models"; Biophysical Journal; bearing a date of Jun. 1997; pp. 2457-2469; vol. 72; Biophysical Society.

Taylor, Dawn M.; Helms Tillery, Stephen I.; Schwartz, Andrew B.; "Research Article: Direct Cortical Control of 3D Neuroprosthetic Devices"; Science; bearing a date of Jun. 7, 2002; pp. 1829-1832; vol. 296; located at: www.sciencemag.org.

"Tiny Robot Reduces Need for Surgery"; Pink Tentacle; bearing a date of Feb. 26, 2007; p. 1; located at http://www.pinktentacle.com/2007/02/tiny-robot-reduces-need-for-surgery; printed on Mar. 8, 2007.

"Trying to control pain can be a double-edged sword, say scientists"; PhysOrg.com; printed on Nov. 2, 2006; pp. 1-2; located at http://www.physorg.com/printnews.php?newsid=81599312.

Tummala, R. Lal; Mukherjee, R.; Aslam, D.; Xi, Ning; Mahadevan, S.; Weng, J.; "Reconfigurable Adaptable Micro-robot"; IEEE; bearing a date of 1999; pp. 687-691.

Twardoch, U.M.; "Integrity of Ultramicro-Stimulation Electrodes Determined from Electrochemical Measurements"; Journal of Applied Electrochemistry; bearing a date of 1994; pp. 835-857; vol. 24; Chapman & Hall.

Warland, David K.; Reinagel, Pamela; Meister, Markus; "Decoding Visual Information from a Population of Retinal Ganglion Cells"; bearing a date of 1997; pp. 2336-2350; The American Physiological Society.

Weis, Rolf; Müller, Bernt; Fromherz, Peter; "Neuron Adhesion on a Silicon Chip Probed by an Array of Field-Effect Transitors"; Physical Review Letters; bearing a date of Jan. 8, 1996; pp. 327-330; vol. 76, No. 2; The American Physical Society.

Wessberg, Johan; Stambaugh, Christopher R.; Kralik, Jerald D.; Beck, Pamela D.; Laubach, Mark; Chapin, John K.; Kim, Jung; Biggs, S. James; Srinivasan, Mandayam A.; Nicolelis, Miguel A.L.; "Letters to Nature: Real-Time Prediction of Hand Trajectory by Ensembles of Cortical Neurons in Primates"; Nature; bearing a date of Nov. 16, 2000; pp. 361-365; vol. 408; Macmillan Magazines Ltd; located at: www.nature com.

White, Dave; "Mini Robot Explores, Gives you Medicine from Within"; Mobile Magazine; bearing a date of Feb. 27, 2007; p. 1; located at: http://www.mobilemag.com/content/100/313/C11869/; printed on Mar. 8, 2007.

Yusa, Go; Muraki, Koji; Takashina, Kei; Hashimoto, Katsushi; Hirayama, Yoshiro; "Controlled multiple quantum coherences of nuclear spins in a nanometre-scale device"; Nature; Apr. 21, 2005; pp. 1001-1005; vol. 434; 2005 Nature Publishing Group; www.nature.com/nature.

"Zyvex NanoEffector Microgrippers"; Nanotechnology at Zyvex; printed on Dec. 7, 2006; pp. 1-2; located at http://www.zyvex.com/Products/Grippers_Features.html.

"Zyvex NanoEffector Microgrippers"; Zyvex.com; bearing a date of 2006; pp. 1-2; Zyvex Corporation.

Korean Intellectual Property Office (KIPO); Notice of Office Action; App. No. 10-2007-7009231; Jun. 8, 2012; pp. 1-5 (translation provided, 2 pages).

UK Intellectual Property Office Examination Report Under Section 18(3); App. No. GB0821526.1; bearing a date of Jul. 15, 2010; pp. 1-2.

Mosby's Dictionary of Medicine, Nursing & Health Professions; "endoscopy"; 2009; Credo Reference. Web. Jun. 29, 2011; 1 page; Elsevier Health Sciences.

U.S. Appl. No. 13/135,696, filed Jul. 12, 2011, Ferren et al.
U.S. Appl. No. 13/135,694, filed Jul. 12, 2011, Ferren et al.
UK Intellectual Property Office Examination Report Under Section 18(3); App. No. GB0821524.6; Aug. 9, 2010; pp. 1-2.
UK Intellectual Property Office Examination Report Under Section 18(3); App. No. GB0821519.6; Aug. 9, 2010; pp. 1-3.
UK Intellectual Property Office Examination Report Under Section 18(3); App. No. GB0821530.3; Aug. 27, 2010; pp. 1-6.
U.S. Appl. No. 13/136,680, Ferren et al.
U.S. Appl. No. 13/136,679, Ferren et al.
U.S. Appl. No. 13/136,677, Ferren et al.
U.S. Appl. No. 13/136,676, Ferren et al.

Arkin, Ronald C.; "Towards the Unification of Navigational Planning and Reactive Control"; Working Notes of the AAAI Spring Symposium on Robot Navigation; bearing dates of Mar. 20-28, 1989; pp. 1-6.

Arleo et al.; "Spatial Cognition and Neuro-Mimetic Navigation: A Model of Hippocampal Place Cell Activity"; bearing a date of Oct. 28, 1999; pp. 1-13.

Balakrishnan et al.; "Spatial Learning and Localization in Rodents: A Computational Model of the Hippocampus and its Implications for Mobile Robots"; Adaptive Behavior; bearing a date of 1999; pp. 173-216 plus cover page; vol. 7, No. 2; SAGE Publications.

Bellin et al.; "Polymeric triple-shape materials"; PNAS; bearing dates of Nov. 18, 2006 and 2006; pp. 18043-18047; vol. 103, No. 48; The National Academy of Sciences of the USA; located at www.pnas.org/cgi/doi/10.1073/pnas.0608586103.

Berman et al.; "Decentralized Autonomous AGV System for Material Handling"; iFirst; bearing a date of Oct. 2002; pp. 3995-4006 (Only the Abstract is being provided); vol. 40, No. 15; located at: http://www.informaworld.com/smpp/content~content=a713846479~db=ai; printed on Apr. 24, 2007.

U.S. Appl. No. 13/136,675, Ferren et al.
U.S. Appl. No. 13/136,678, Ferren et al.
U.S. Appl. No. 13/136,674, Ferren et al.

Bianco et al.; "Carbon Nanotube-based Vectors for Delivering Immunotherapeutics and Drugs"; Nanotechnologies for the Live Sciences: Nanomaterials for Medical Diagnosis and Therapy; bearing a date of 2007; Chapter 3; pp. 85-142.; vol. 10; Wiley-VCH Verlag GmbH & Co. KGaA; Weinheim.

Breslin et al.; "Autofluorescence and Diffuse Reflectance Properties Malignant and Benign Breast Tissues"; Annals of Surgical Oncology; bearing dates of 2003 and 2004; pp. 65-70; vol. 11, No. 1; Lippincott Williams & Wilkin.

Bright et al.; "Automated Pipe Inspection Robot"; Industrial Robot: An International Journal; bearing a date of Aug. 1997; pp. 285-289 (Only the Abstract is being provided); vol. 24, No. 4; located at: http://www.emeraldinsight.com/10.1108/01439919710176372; printed on Apr. 23, 2007.

Brinn, David; "A incredible journey from an Israeli robotics team"; ISRAEL21c: A Focus Beyond; bearing a date of Nov. 12, 2006; pp. 1-3; ISRAEL21c.org.

Brown et al.; "Performance Test Results of an Integrated GPS/MEMS Inertial Navigation Package"; Proceedings of ION GNSS 2004, bearing a date of Sep. 2004; pp. 1-8.

Budgett et al.; "Novel technology for the provision of power to implantable physiological devices"; Journal of Applied Physiology; bearing dates of Jan. 27, 2006, Jan. 5, 2007, and 2007; pp. 1658-1663; vol. 102; The American Physiological Society.

Bullitt et al.; "Analysis of Time-Varying Images Using 3D Vascular Models"; Proceedings 30th Applied Imagery Pattern Recognition Workshop; bearing a date of Apr. 2001; pp. 9-14; IEEE Computer Society; Piscataway, NJ.

Burke et al.; "Towards a single-chip, implantable RFID system: is a single-cell radio possible?"; Biomed Microdevices; bearing a date of 2009; pp. 1-8; Springer.

Cady et al.; "Optimized linkage and quenching strategies for quantum dot molecular beacons"; Molecular and Cellular Probes; bearing dates of Jul. 5, 2006, Sep. 7, 2006, Sep. 17, 2006, 2006, and 2007; pp. 116-124; vol. 21; Elsevier Ltd.

Cavalcanti et al.; "Autonomous Multi-Robot Sensor-Based Cooperation for Nanomedicine"; Nanotechnology Special Edition; bearing a date of Aug. 2002; pp. 1-4; International Journal of Nonlinear Science and Numerical Stimulation.

Chen et al.; "Review on the Achievements in Simultaneous Localization and Map Building for Mobile Robot" CSA Illumina; bearing a date of Jun. 2005; pp. 455-460 (Only the Abstract is being provided); vol. 22, No. 3; ProQuest-CSA LLC; located at: http://md1.csa.com/partners/viewrecord.php?requester=gs&collection=TRD&recid=A056354818AH&recid=2005134422784EA&q=Review+on+the+Achievements+in+Simultaneous+Localization+and+Map+Building+for+Mobile+Robot&uid=790366044&setcookie=yes.

Chiyo et al.; "Effective detection of bronchial preinvasive lesions by a new autofluorescence imaging bronchovideoscope system"; Lung Cancer; bearing dates of May 12, 2004, Nov. 17, 2004, Nov. 23, 2004, 2004, and 2005; pp. 307-313; vol. 48; Elsevier Ireland Ltd.

Chung et al.; "Advanced Optical Imaging Requiring No Contrast Agents—A New Armamentarium for Medicine and Surgery"; Current Surgery; bearing dates of May/Jun. 2005 and 2005; pp. 365-370; vol. 62, No. 3; Elsevier Inc.

Dacosta et al.; "Autofluorescence characterisation of isolated whole crypts and primary cultured human epithelial cells from normal, hyperplastic, and adenomatous colonic mucosa"; Journal of Clinical Pathology; bearing dates of 2004 and 2005; pp. 766-774; vol. 58.

Degani et al.; "Minimalistic, Dynamic, Tube Climbing Robot"; 2010 IEEE International Conference on Robotics and Automation; bearing dates of May 3-8, 2010 and 2010; pp. 1100-1101; IEEE.

Desouza et al.; "Vision for Mobile Robot Navigation: A Survey"; IEEE Transactions on Pattern Analysis and Machine Intelligence; bearing a date of Feb. 2002; pp. 237-267 (Only the Abstract is being provided); vol. 24, No. 2; located at: http://csdl2.computer.org/persagen/DLAbsToc.jsp?resourcePath=/dl/trans/tp/&toc=comp/trans/tp/2002/02/i2toc.xml&DOI=10.1109/34.982903; printed on Apr. 23, 2007.

Diard et al.; "A theoretical comparison of probabilistic and biomimetic models of mobile robot navigation"; Proceedings of the 2004 IEEE International Conference on Robotics & Automation; bearing dates of Apr. 2004 and 2004; pp. 933-938; IEEE.

Dweik et al.; "Exhaled breath analysis: the new frontier in medical testing"; Journal of Breath Research; bearing a date of 2008; pp. 1-3; vol. 2; IOP Publishing Ltd; UK.

Edwards, Lin; "Spider pill to seek out disease"; PhysOrg.com; bearing dates of Oct. 16, 2009 and 2009; p. 1.

Eker et al.; "Clinical spectral characterisation of colonic mucosal lesions using autofluorescence and δ aminolevulinic acid sensitization"; Gut; bearing dates of 1998 and 1999; pp. 511-518; vol. 44.

Eulenstein et al.; "Ultrasound-Based Navigation System Incorporating Preoperative Planning for Liver Surgery"; International Congress Series CARS 2004—Computer Assisted Radiology and Surgery, Proceedings of the 18$^{th}$ International Congress and Exhibition; bearing a date of 2004; pp. 758-763; vol. 1268.

Filliat et al.; "Map Based Navigation in Mobile Robots: I. A Review of Localization Strategies"; Science Direct-Cognitive Systems Research; bearing dates of Feb. 12, 2003 and Dec. 2003; pp. 1-58; vol. 4, No. 4; Elsevier Science.

Foxlin et al.; "Miniature 6-DOF inertial system for tracking HMDs"; Helmet and Head-Mounted Displays III, AeroSense 98; bearing dates of Apr. 13-14, 1998; pp. 1-15; vol. 3362; SPIE.

Gabrecht et al.; "Detection of early bronchial cancer by autofluorescence: results in patients with H&N cancer"; Diagnostic Optical Spectroscopy in Biomedicine IV, Proc. SPIE-OSA Biomedical Optics; bearing a date of 2007; pp. 1-8; vol. 6628; SPIE-OSA.

Gao et al., "A Micro Sensing Probe for Detecting Individual Biological Cells"; Proceedings of the 25$^{th}$ Annual International Conference of the IEEE EMBS; bearing dates of Sep. 17-21, 2003 and 2003; pp. 3348-3351; IEEE.

Gillenwater et al.; "Noninvasive Diagnosis of Oral Neoplasia Based on Fluorescence Spectroscopy and Native Tissue Autofluorescence"; Archives of Otolaryngology-Head & Neck Surgery; bearing a date of Nov. 1998 and 1998; pp. 1251-1258; vol. 124.

Grifantini, Kristina; "Voyage of the Bacteria Bots"; Technology Review; bearing a date of Oct. 31, 2008; pp. 1-4; Technology Review.

Groothuis et al.; "The entry of antiviral and antiretroviral drugs into the central nervous system"; Journal of NeuroVirology; bearing a date of 1997; pp. 387-400; vol. 3; Journal of NeuroVirology, Inc.

"Guessing Robots Predict Their Environments, Navigate Better"; PhysOrg.com; printed on Sep. 16, 2008; pp. 1-2; original story found at www.phyorg.com/news100887209.html.

Gur, Amir; "The Nanobots are Coming"; TFOT; bearing a date of Jul. 9, 2007; pp. 1-2; The Future of Things.

Hattori, Kevin; "Robot Can Crawl Through Human Body"; American Technion Society; bearing a date of Jul. 7, 2009; pp. 1-2; American Technion Society; located at http:/www.ats.org/site/News2?page=NewsArticle&id=6063&news_iv_ctrl=1161&printer_friendly=1.

Herth et al.; "Successful Bronchoscopic Placement of Tracheobronchial Stents Without Fluoroscopy*"; Chest; bearing a date of Jun. 2001; pp. 1910-1912; vol. 119, No. 6; American College of Chest Physicians.

Hertzberg et al.; "Landmark-Based Autonomous Navigation in Sewerage Pipes"; Proceedings of EUROBOT; bearing a date of 1996; pp. 68-73; IEEE.

Hirsch et al.; "A new device with PZT ultrasonic transducers in MEMS technology"; Journal of Physics: Conference Series 34, International MEMS Conference 2006; bearing a date of 2006; pp. 475-480; IOP Publishing Ltd.

Hollings et al.; "Diagnostic imaging of lung cancer"; European Respiratory Journal; bearing a date of 2002, pp. 722-742; vol. 19; ERS Journals Ltd.

Hornyak, Tim; "RFID Powder"; Scientific American Magazine; bearing dates of Feb. 2008 and 2008; pp. 68-71; Scientific American, Inc.

Hosseini-Khayat, Saied; "A Lightweight Security Protocol for Ultra-low Power ASIC Implementation for Wireless Implantable Medical Devices"; 2011 Symposium on Medical Information and Communication Technology (ISMICT); bearing dates of 2011 and Mar. 27-30, 2011; pp. 6-9; IEEE.

Howell et al.; "Practical Mobile Robot Self-Localization"; Proceedings of the IEEE International Conference on Robotics and Automation, 2000; bearing dates of Apr. 24-28, 2000; pp. 3485-3492; vol. 4.

Jaiswal et al.; "Long-term multiple color imaging of live cells using quantum dot bioconjugates"; Nature Biotechnology; bearing dates of Jan. 2003 and 2003; pp. 47-51; vol. 21; Nature Publishing Group.

Jovanov et al.; "A wireless body area network of intelligent motion sensors for computer assisted physical rehabilitation"; Journal of NeuroEngineering and Rehabilitation; bearing dates of Mar. 1, 2005, Jan. 28, 2005, Mar. 1, 2005, and 2005; pp. 1-10; vol. 2, No. 6; BioMed Central Ltd.

Karino et al.; "Flow Patterns in Vessels of Simple and Complex Geometriesa"; Annals of the New York Academy of Sciences; bearing a date of 1987; pp. 422-441; vol. 516.

Kawaguchi et al.; "Internal Pipe Inspection Robot"; IEEE Xplore; bearing dates of May 21, 1995-May 27, 1995 and 2005; pp. 857-862 (Only the Abstract is being provided); vol. 1; IEEE; located at: http://ieeexplore.ieee.org/xpls/abs_all.jsp?rnumber=525390; printed on Apr. 23, 2007.

Kharitonov et al.; "Exhaled Markers of Pulmonary Disease"; American Journal of Respiratory and Critical Care Medicine; bearing dates of Sep. 5, 2000, Jan. 24, 2001, and 2001; pp. 1693-1722; vol. 163.

Kim et al.; "Inchworm-Like Microbot for Capsule Endoscope"; Proceedings of the 2004 IEEE International Conference on Robotics and Biomimetics; bearing dates of Aug. 22-26, 2004 and 2004; pp. 458-463; IEEE.

Kim et al.; "Ultrasensitive carbon nanotube-based biosensors using antibody-binding fragments"; Analytical Biochemistry; bearing a date of 2008; pp. 193-198; vol. 381; Elsevier Inc.

Kirchner et al.; "A Prototype Study of an Autonomous Robot Platform for Sewerage System Maintenance"; Autonomous Robots; bearing a date of 1997; pp. 319-331; vol. 4; Kluwer Academic Publishers.

Kitaoka et al.; "A three-dimensional model of the human airway tree"; Journal of Applied Physiology; bearing a date of 1999; pp. 2207-2217; vol. 87; The American Physiological Society.

Kitching, John; "Time for a Better Receiver: Chip-Scale Atomic Frequency References"; GPS World; bearing a date of Nov. 2007; pp. 52-57.

Knappe, Svenja; "Emerging Topics: MEMS Atomic Clocks"; Comprehensive Microsystems; bearing a date of 2007; pp. 571-612; vol. 3; Elsevier B.V.; Netherlands.

Koenig et al.; "Laser-Induced Autofluorescence for Medical Diagnosis"; Journal of Fluorescence; bearing a date of 1994, pp. 17-40; vol. 4, No. 1; Plenum Publishing Corporation.

Kuipers et al.; "A Robot Exploration and Mapping Strategy Based on a Semantic Hierarchy of Spatial Representations"; Robotics and Autonomous Systems; bearing a date of 1981; pp. 47-63; vol. 8; Elsevier Science Publishers B.V.

Kuntze et al.; "Experiences With the Development of a Robot for Smart Multisensoricpipe Inspection"; IEEE Xplore; bearing dates of May 16, 1998-May 20, 1998 and 2005; pp. 1773-1778 (Only the Abstract is being provided); vol. 2; IEEE; located at: http://ieeexplore.ieee.org/xpls/abs_all.jsp?rnumber=677423; printed on Apr. 23, 2007.

Latombe, Jean-Claude; "Chapter 1: Introduction and Overview"; Robot Motion Planning; bearing a date of 1991; 11 pages total, pp. 12-20; Kluwer Academic Publishers.

Laumond et al.; "Robot Motion Planning and Control"; bearing a date of 1998; pp. 1-343 plus cover page, foreword and table of contents (353 total pages); Springer.

Leong et al.; "Tetherless thermobiochemically actuated microgrippers"; PNAS; bearing dates of Jan. 20, 2009 and 2009; pp. 703-708; vol. 106, No. 3; The National Academy of Sciences of the USA; located at www.pnas.org_cgi_doi_10.1073_pnas.0807698106.

Luckevich, Mark, "MEMS microvalves: the new valve world"; Valve-World; bearing a date of May 2007; pp. 79-83.

Lynch et al.; "Design of Piezoresistive MEMS-Based Accelerometer for Integration with Wireless Sensing Unit for Structural Monitoring"; Journal of Aerospace Engineering; bearing a date of Jul. 2003; pp. 108-114; vol. 3; ASCE.

Machado et al., "Detection of Lung Cancer by Sensor Array Analyses of Exhaled Breath"; American Journal of Respiratory and Critical Care Medicine; bearing a date of 2005; pp. 1286-1291; vol. 171.

Marcu et al.; "In vivo detection of macrophages in a rabbit atherosclerotic model by time-resolved laser-induced fluorescence spectroscopy"; Atherosclerosis; bearing a date of 2005; pp. 295-303; vol. 181; Elsevier Ireland Ltd.

Martel, Sylvain; "Fundamental Principles and Issues of High-speed Piezoactuated Three-legged Motion for Miniature Robots Designed for Nanometer-scale Operations"; The International Journal of Robotics Research; bearing dates of Jul. 2005 and 2005; pp. 575-588; vol. 24, No. 7; Sage Publications.

Mataric, Maja J.; "Integration of Representation into Goal-Driven Behavior-Based Robots"; IEEE Transactions on Robotics and Automation; bearing dates of Jun. 1992 and 1992; pp. 304-312; vol. 8, No. 3; IEEE.

Mattley et al.; "Blood Characterization using uv/vis Spectroscopy"; Advances in Fluorescence Sensing Technology II (Proceedings Volume); bearing a date of 1995; pp. 462-470; vol. 2388; SPIE.

Mehmood et al.; "Autonomous Navigation of Mobile Agents Using RFID-Enabled Space Partitions"; ACMGIS '08; bearing dates of Nov. 5-7, 2008 and 2008; pp. 1-10; ACM.

Menciassi et al.; "Towards Active Capsular Endoscopy: Preliminary Results on a Legged Platform"; Proceedings of the 28$^{th}$ IEEE EMBS Annual International Conference; bearing dates Aug. 30, 2006-Sep. 3, 2006 and 2006; pp. 2215-2218; IEEE.

Meyer et al.; "Map-Based Navigation in Mobile Robots: II. A Review of Map-Learning and Path-Learning Strategies"; Science Direct-Cognitive Systems Research; bearing dates of Feb. 12, 2003 and Dec. 4, 2003; pp. 1-51; vol. 4, No. 4; Elsevier Science.

Mohan et al., "Bokode: Imperceptible Visual tags for Camera Based Interaction from a Distance"; ACM Transactions on Graphics (Proceedings of SIGGRAPH 2009); bearing dates of Aug. 3-7, 2009; pp. 1-8.

Mok et al.; "Recent Progress in Nucleic Acid Aptamer-Based Biosensors and Bioassays"; Sensors; bearing a date of 2008; pp. 7050-7084; vol. 8.

Morrison et al., "Clinical Applications of Micro- and Nanoscale Biosensors"; Biomedical Nanostructures; bearing a date of 2008; Chapter 17; pp. 433-454; John Wiley & Sons, Inc.

Motomiya et al.; "Flow Patterns in the Human Carotid Artery Bifurcation"; Stroke; bearing dates of Jan.-Feb. 1984; pp. 50-56; vol. 15, No. 1.

Nehmzow et al.; "Robot Navigation in the Real World: Experiments with Manchester's *FortyTwo* in Unmodified, Large Environments"; Robotics and Autonomous Systems; bearing a date of 2000; pp. 223-242; vol. 33; Elsevier Science B.V.

Nguyen, Clark T.-C.; "MEMS Technology for Timing and Frequency Control"; IEEE Transactions on Ultrasonics, Ferroelectrics, and Frequency Controls; bearing dates of Feb. 2007 and 2007; pp. 251-270; vol. 54, No. 2; IEEE.

Nordstrom et al.; "Identification of Cervical Intraepithelial Neoplasia (CIN) Using UV-Excited Fluorescence and Diffuse-Reflectance Tissue Spectroscopy"; Lasers in Surgery and Medicine; bearing a date of 2001; pp. 118-127; vol. 29; Wiley-Liss, Inc.

Nowinski et al.; "Three-dimensional Atlas of the Brain Anatomy and Vasculature"; RadioGraphics; bearing dates of Jan.-Feb. 2005 and 2005; pp. 263-271; vol. 25, No. 1; RSNA.

Pan et al.; "A magnetically driven PDMS micropump with ball checkvalves"; Journal of Micromechanics and Microengineering; bearing a date of 2005, pp. 1021-1026; vol. 15; IOP Publishing Ltd.

Pavlidis, N.; "The diagnostic and therapeutic management of leptomeningeal carcinomatosis"; Annals of Oncology; bearing a date of 2004; pp. iv285-iv291; vol. 15 (Supp. 4); European Society for Medical Oncology.

Peng et al.; "Ultraviolet light-emitting diodes operating in the 340 nm wavelength range and application to time-resolved fluorescence spectroscopy"; Applied Physics Letters; bearing dates of Aug. 23, 2004 and 2004; pp. 1436-1438; vol. 85, No. 8; American Institute of Physics.

Pfister et al.; "Weighted Line Fitting Algorithms for Mobile Robot Map Building and Efficient Data Representation"; Proceedings of the 2003 IEEE International Conference on Robotics and Automation; bearing a date of Sep. 14-19, 2003; pp. 1-8.

"Philips develops "intelligent pill""; Reuters; bearing a date of Nov. 11, 2008; p. 1; Thomson Reuters.

"Philips' intelligent pill targets drug development and treatment for digestive tract diseases"; PhysOrg.com; bearing a date of Nov. 11, 2008; pp. 1-3; located at http://www.physorg.com/news145640874.html.

Phillips et al.; "Detection of Lung Cancer With Volatile Markers in the Breath"; Chest; bearing dates of Jun. 2003 and 2003; pp. 2115-2123; vol. 123, No. 6; American College of Chest Physicians.

Pisupati et al.; "A Central Axis Algorithm for 3D Bronchial Tree Structures"; Proceedings of the International Symposium on Computer Vision; bearing a date of 1995; pp. 259-264; IEEE.

Psathakis et al.; "8-Isoprostane, a Marker of Oxidative Stress, Is Increased in the Expired Breath Condensate of Patients With Pulmonary Sarcoidosis"; Chest; bearing dates of Mar. 2004 and 2004, pp. 1005-1011; vol. 125, No. 3; American College of Chest Physicians.

Quaglia et al.; "An endoscopic capsule robot: a meso-scale engineering case study"; Journal of Micromechanics and Microengineering; bearing a date of 2009; pp. 1-11; vol. 19; IOP Publishing Ltd.

Quirini et al.; "Design of a Pill-Sized 12-legged Endoscopic Capsule Robot"; 2007 IEEE International Conference on Robotics and Automation; bearing dates of Apr. 10-14, 2007 and 2007; pp. 1856-1862; IEEE.

Raman et al.; "In Vivo Atherosclerotic Plaque Characterization Using Magnetic Susceptibility Distinguishes Symptom-Producing Plaques"; JACC: Cardiovascular Imaging; bearing dates of Jan. 2008 and 2008; pp. 49-57; vol. 1, No. 1; Elsevier.

Rasmussen et al.; "Proximity-based Access Control for Implantable Medical Devices"; CCS '09, Proceedings of the 16$^{th}$ ACM Conference on Computer and Communications Security; bearing dates of Nov. 9-13, 2009 and 2009; pp. 1-10.

"Remote-controlled capsule endoscope safely examines the stomach"; PhysOrg.com; bearing a date of Jan. 18, 2011; pp. 1-2; located at http://www.physorg.com/news-2011-01-remote-controlled-capsule-endoscope-safety-stomach.html.

"Researchers Create Tiny, Self-Propelled Devices"; PhysOrg.com; printed on Feb. 12, 2007; pp. 1-3; located at: http://www.physorg.com/printnews.php?newsid=90521279.

Roh et al.; "Strategy for Navigation Inside Pipelines With Differential-Driveinpipe Robot"; IEEE Xplore; 2002 and 2005; pp. 2575-2580 (Only the Abstract is being provided); vol. 3; IEEE; located at: http://ieeexplore.ieee.org/xpls/abs_all.jsp?arnumber=1013619; printed on Apr. 23, 2007.

Roh et al.; "Actively Steerable In-Pipe Inspection Robots for Underground Urban Gas Pipelines"; IEEE Xplore; bearing dates of 2001 and 2005; pp. 761-766 (Only the Abstract is being provided); vol. 1; IEEE; located at: http://ieeexplore.ieee.org/xpls/abs_all.jsp?arnumber=932642; printed on Apr. 23, 2007.

Rolfe, Brigitte; "Toward Nanometer-Scale Sensing Systems: Natural and Artificial Noses as Models for Ultra-Small, Ultra-Dense Sensing Systems"; Advances in Computers; bearing dates of Nov. 2004, 2004, and 2007; pp. 11-46; vol. 71; Elsevier, B.V.

Schertler et al.; "Effects of ECG Gating and Postprocessing Techniques on 3D MDCT of the Bronchial Tree"; AJR; bearing a date of Jul. 2004; pp. 83-89; vol. 183; American Roentgen Ray Society.

Schnakenberg et al.; "Intravascular pressure monitoring system"; Sensors and Actuators A: Physical; bearing a date of 2004; pp. 61-67; vol. 110; Elsevier B.V.

Schwartz, John; "In the Lab: Robots That Slink and Squirm"; The New York Times: Science; bearing a date of Mar. 27, 2007; pp. 1-4; The New York Times Company; located at: http://www.nytimes.com/2007/03/27/science/27robo.html?ex=1332648000&en=d4541141c174b454&ei=5124&partner=digg&exprod=digg; printed on Mar. 27, 2007.

"Spider pill to seek out diseases"; PhysOrg.com; bearing a date of Oct. 16, 2009 and 2009; p. 1; located at http://www.physorg.com/news174893082.html.

Sun et al.; "A Miniature RF Communication System for Micro Gastrointestinal Robots"; Journal of Medical Engineering & Technology; bearing a date of 2003; pp. 160-163; vol. 27.

Suzumori et al.; "Micro Inspection Robot for 1-in Pipes"; IEEE/ASME Transactions on Mechatronics; bearing dates of Sep. 1999 and 1999; pp. 286-292; vol. 4, No. 3; IEEE.

Tang et al.; "Cerebral Vascular Tree Matching of 3D-RA Data Based on Tree Edit Distance"; Medical Imaging and Augmented Reality; bearing a date of 2006; pp. 116-123.

The Biomedical Engineering Handbook, Second Edition; bearing a date of 2000; pp. IV-1—43-31; vol. I; CRC Press LLC.

The Biomedical Engineering Handbook, Second Edition; bearing a date of 2000; pp. V-1—51-9; vol. I; CRC Press LLC.

Thrun, Sebastian; "Learning Metric-Topological Maps for Indoor Mobile Robot Navigation"; Artificial Intelligence; bearing a date of 1998; pp. 21-71; vol. 99; Elsevier Science B.V.

Thrun, Sebastian; "Probabilistic Algorithms in Robotics"; AI Magazine; bearing dates of Winter 2000 and 2000; pp. 93-109; vol. 21, No. 4; American Association for Artificial Intelligence.

Thrun, Sebastian; "Robotic Mapping: A Survey"; Exploring Artificial Intelligence in the New Millenium; bearing a date of Feb. 2002; pp. 1-29 (31 total pages); Morgan Kaufmann.

Thrun et al.; "A Real-Time Algorithm for Mobile Robot Mapping With Applications to Multi-Robot and 3D Mapping"; IEEE International Conference on Robotics and Automation; bearing a date of Apr. 2000; pp. 1-8.

Thrun et al.; "Integrating Topological and Metric Maps for Mobile Robot Navigation: A Statistical Approach"; pp. 1-7.

Tomatis et al.; "Simultaneous Localization and Map Building: A Global Topological Model with Local Metric Maps"; Robotics Autonomous Systems; bearing a date of 2003; pp. 1-6; vol. 44.

Tsuruta et al.; "Control Circuit in an In-Pipe Wireless Micro Inspection Robot"; IEEE Xplore; bearing dates of 2000 and 2005; pp. 59-64 (Only the Abstract is being provided); IEEE; located at: http://ieeexplore.ieee.org/xpls/abs_all.jsp?arnumber=903290; printed on Apr. 23, 2007.

Ulrich et al.; "Appearance-Based Place Recognition for Topological Localization"; IEEE International Conference on Robotics and Automation; bearing a date of Apr. 2000; pp. 1023-1029.

Verheye et al.; "Selective Clearance of Macrophages in Atherosclerotic Plaques by Autophagy"; Journal of the American College of Cardiology; bearing dates of Feb. 13, 2007 and 2007; pp. 706-715; vol. 49, No. 6; Elsevier Inc.

Wacharasindhu et al.; "Radioisotope microbattery based on liquid semiconductor"; Applied Physics Letters; bearing dates of Dec. 11, 2008, Jun. 9, 2009, Jul. 6, 2009, Dec. 8, 2009 and 2009; pp. 014103-1-014103-3; vol. 95; American Institute of Physics.

Wakimoto et al.; "A Micro Snake-Like Robot for Small Pipe Inspection"; International Symposium on Micromechatronics and Human Science; bearing a date of 2003; pp. 303-308; IEEE.

Wang et al.; "A MEMS-based Air Flow Sensor with a Free-standing Micro-cantilever Structure"; Sensors; bearing dates of Aug. 27, 2007, Oct. 10, 2007, Oct. 17, 2007, and 2007; pp. 2389-2401; vol. 7; MDPI.

Watson et al.; "Piezoelectric ultrasonic resonant motor with stator diameter less than 250 µm: the *Proteus* motor"; Journal of Micromechanics and Microengineering; bearing dates of Sep. 25, 2008, Nov. 18, 2008, Jan. 20, 2009, and 2009; pp. 1-5; vol. 19; IOP Publishing Ltd.

Weingandt et al.; "Autofluorescence spectroscopy for the diagnosis of cervical intraepithelial neoplasia"; BJOG: an International Journal of Obstetrics and Gynaecology; bearing dates of Aug. 2002 and 2002; pp. 947-951; vol. 109; RCOG.

Xi et al.; "Self-assembled microdevices driven by muscle"; Nature Materials; bearing dates of Feb. 2005 and 2005; pp. 180-184 (10 pages total); vol. 4; Nature Publishing Group.

Yang et al.; "Power generation with laterally packaged piezoelectric fine wires"; Nature Nanotechnology; bearing dates of Nov. 9, 2008, Jan. 2009, and 2009; pp. 34-39; vol. 4; Macmillan Publishers Limited.

Yang et al.; "Converting Biomechanical Energy into Electricity by a Muscle-Movement-Driven Nanogenerator"; Nano Letters; bearing dates of Dec. 25, 2008, Jan. 31, 2009, and 2009; pp. 1201-1205; vol. 9, No. 3; American Chemical Society.

Yu et al.; "System for the analysis and visualization of large 3D anatomical trees"; Computers in Biology and Medicine; bearing dates of Oct. 6, 2006, May 31, 2007, Jun. 4, 2007, and 2007; pp. 1802-1820; vol. 37; Elsevier Ltd.

Zhao et al.; "Physicist Develops Natural Motor Technique"; PhysOrg.com; bearing dates of Apr. 21, 2007 and 2007; 1 page; United Press International; located at: http://www.physorg.com/news96357975.html; printed on Apr. 23, 2007.

Zheng et al.; "Design and Fabrication of a Micro Coulter Counter with Thin Film Electronics"; Proceedings of 2006 International Conference on Microtechnologies in Medicine and Biology; bearing dates of May 9-12, 2006 and 2006; pp. 16-19; IEEE.

Zhu et al.; "Flattening Maps for the Visualization of Multibranched Vessels"; IEEE Transactions on Medical Imaging; bearing dates of Feb. 10, 2004, Sep. 27, 2004, Feb. 2005, and 2005; pp. 191-198; vol. 24, No. 2; IEEE.

Zrimec et al.; "3D Modelling and Visualization of the Human Lung"; Proceedings of the 2nd International Symposium on 3D Data Processing, Visualization, and Transmission (3DPVT'04); bearing a date of 2004; pp. 110-115; IEEE.

Zyga, Lisa; "Microswimmer Propels Itself With Near-Zero Friction"; PhysOrg.com; bearing dates of Jun. 4, 2007 and 2007; pp. 1-2; PhyOrg.com; located at: http://www.physorg.com/news100176842.html; printed on Jun. 6, 2007.

Japanese Patent Office: Office Action; Japanese App. No. 2007-533572; Sep. 22, 2010; pp. 1-4.

UK Intellectual Property Office Examination Report Under Section 18(3); App. No. GB0821519.6; Oct. 19, 2010; 1 page.

UK Intellectual Property Office Combined Search and Examination Report Under Sections 17 & 18(3); App. No. GB1016383.0; Nov. 1, 2010; pp. 1-4.

\* cited by examiner

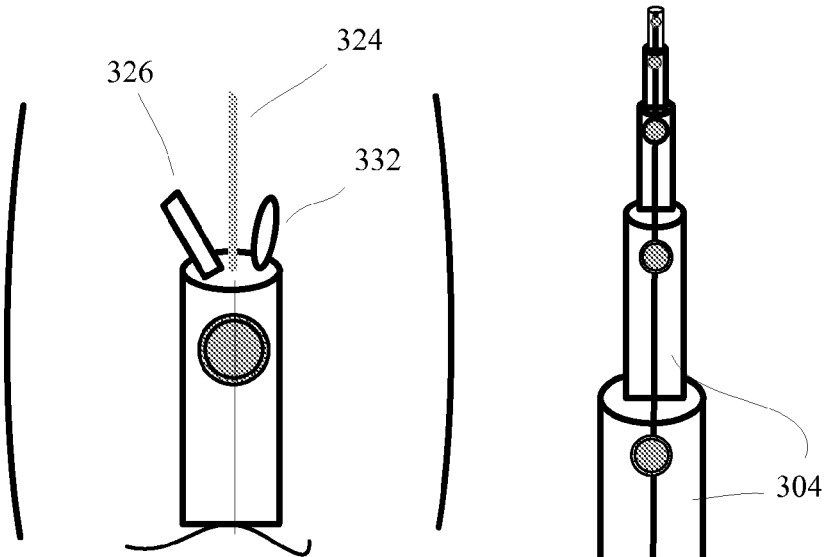
FIG. 3A
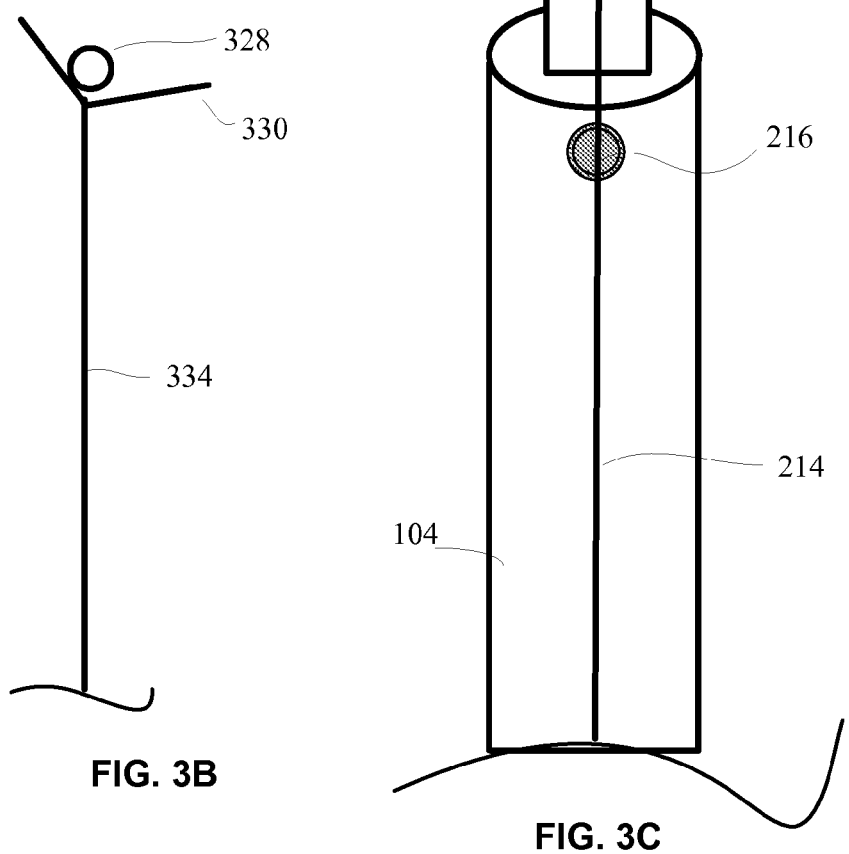
FIG. 3B
FIG. 3C

SYSTEM FOR PERFUSION MANAGEMENT

CROSS-REFERENCE TO RELATED APPLICATIONS

The present application is related to, claims the earliest available effective filing date(s) from the following listed application(s) (the "Related Applications") (e.g., claims earliest available priority dates for other than provisional patent applications or claims benefits under 35 USC § 119(e) for provisional patent applications), and incorporates by reference in its entirety all subject matter of the following listed applications(s) to the extent such subject matter is not inconsistent herewith; the present application also claims the earliest available effective filing date(s) from, and also incorporates by reference in its entirety all subject matter of any and all parent, grandparent, great-grandparent, etc. applications of the "Related Application(s)."

RELATED APPLICATIONS

1. For purposes of the USPTO extra-statutory requirements, the present application constitutes a continuation-in-part of U.S. patent application Ser. No. 10/827,572, entitled A SYSTEM WITH A RESERVOIR FOR PERFUSION MANAGEMENT, naming Lowell L. Wood, Jr. as inventor, filed 19 Apr. 2004, which is currently co-pending, or is an application of which a currently co-pending application is entitled to the benefit of the filing date.

2. For purposes of the USPTO extra-statutory requirements, the present application constitutes a continuation-in-part of U.S. patent application Ser. No. 10/827,578, entitled A SYSTEM WITH A SENSOR FOR PERFUSION MANAGEMENT, naming Lowell L. Wood, Jr. as inventor, filed 19 Apr. 2004, which is currently co-pending, or is an application of which a currently co-pending application is entitled to the benefit of the filing date.

3. For purposes of the USPTO extra-statutory requirements, the present application constitutes a continuation-in-part of U.S. patent application Ser. No. 10/827,390, entitled A TELESCOPING PERFUSION MANAGEMENT SYSTEM, naming Lowell L. Wood, Jr. as inventor, filed 19 Apr. 2004, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present application relates, in general, to detection and/or treatment.

SUMMARY

In one aspect, a system includes, but is not limited to at least one arm; a control circuit coupled to said at least one arm; at least one receptacle coupled to said at least one arm; and at least one sensor coupled to said at least one arm, said system configured for implantation in an animal. In addition to the foregoing, other system aspects are described in the claims, drawings, and text forming a part of the present application.

In one aspect, a method includes but is not limited to: making a device, by providing a cavity for storing a receivable; and including at least one transmitting channel coupled to said cavity for delivering said receivable from said cavity to a predetermined location in an animal, cooperative with a monitoring system and a detecting system including logic or software operative for delivering said receivable. In addition to the foregoing, other method aspects are described in the claims, drawings, and text forming a part of the present application.

In another aspect, a method includes but is not limited to: placing a device comprising a receiving unit for storing a deliverable and in communication with a pliable duct; directing said pliable duct to a location; and administering said deliverable from said receiving unit to said location cooperative with a guiding system and a detecting system. In addition to the foregoing, other method aspects are described in the claims, drawings, and text forming a part of the present application.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In addition to the foregoing, various other method and or system aspects are set forth and described in the text (e.g., claims and/or detailed description) and/or drawings of the present application.

The foregoing is a summary and thus contains, by necessity; simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the non-limiting detailed description set forth herein.

BRIEF DESCRIPTION OF THE FIGURES

FIGS. 3A, 3B, and 3C show exploded views of various aspects of the device of FIG. 1, including an extensible finger 104.

The use of the same symbols in different drawings typically indicates similar or identical items.

DETAILED DESCRIPTION

The present application uses formal outline headings for clarity of presentation. However, it is to be understood that the outline headings are for presentation purposes, and that different types of subject matter may be discussed throughout the application (e.g., device(s)/structure(s) may be described under the process(es)/operations heading(s) and/or process(es)/operations may be discussed under structure(s)/process(es) headings). Hence, the use of the formal outline headings is not intended to be in any way limiting.

1. Perfusion Management Device(s) and/or Process(es).

Figure 1:
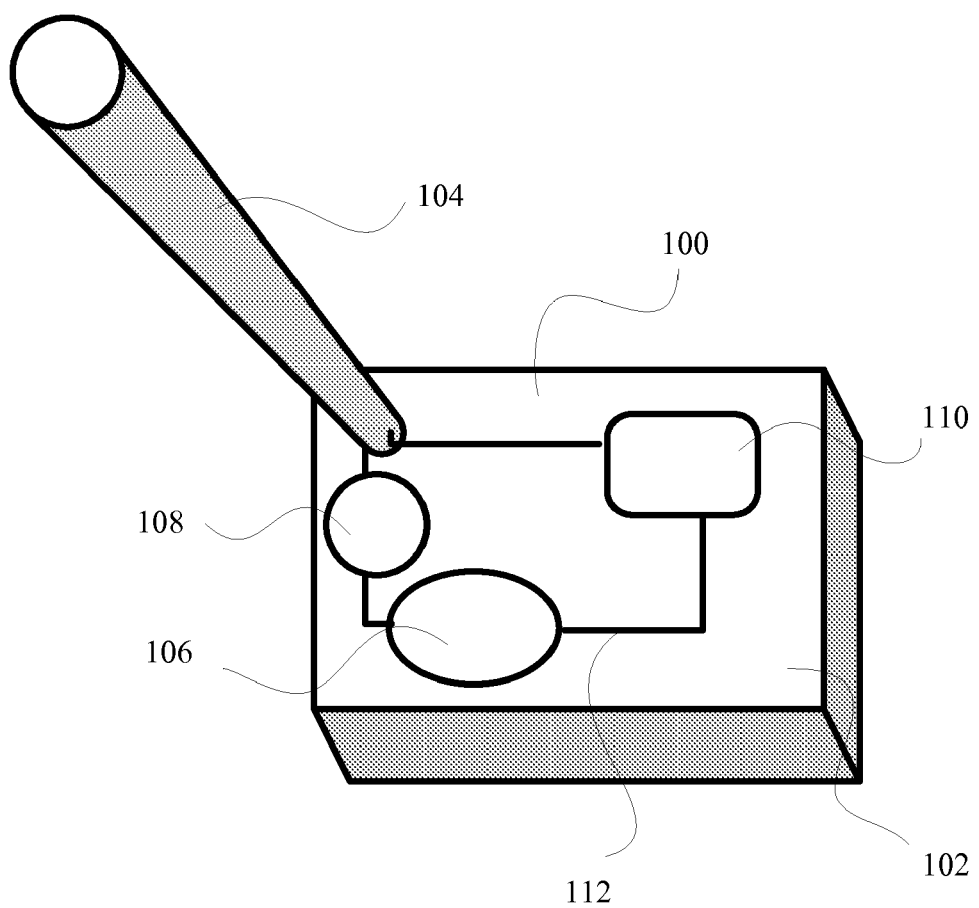
FIG. 1 is a front-plan view of a device for perfusion management 100.

With reference now to FIG. 1, shown is a front plan view illustrative of various exemplary perfusion management device(s) and/or process(es). Accordingly, the present application first describes certain specific exemplary structures of FIG. 1; thereafter, the present application illustrates certain specific exemplary processes. Those having skill in the art will appreciate that the specific devices and processes described herein are intended as merely illustrative of their more general counterparts.

A. Structure(s) and or Device(s)

With reference to the figures, and with reference now to FIG. 1, shown is a front-plan view of a device for perfusion management 100. The device for perfusion management 100 includes a body portion 102 from which at least one arm 104 projects. A receptacle 106 within the body portion 102 contains a fluid, for example, a fluid for treatment. A controllable valve 108 provides a path through which the fluid may travel to the at least one arm 104.

A control circuit 110 provides a control signal that may open or close the control valve 108. The control circuit 110 may be connected to a sense line 112 that allows it to monitor the fluid levels within the receptacle 106. Additionally, a sense line 114 connects the control circuit 110 to a sensor 116 at the distal end of the at least one arm 104.

Figure 2:
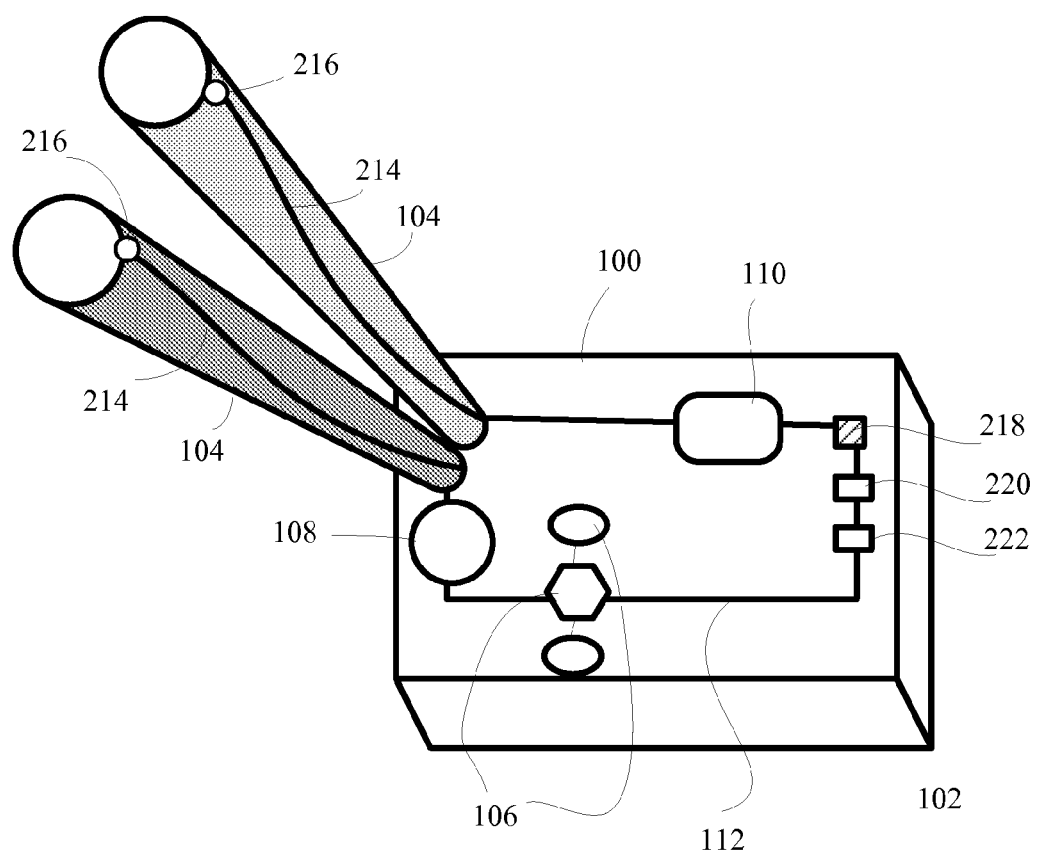
FIG. 2 is a front-plan view of another aspect of the device for perfusion management 100.

Referring now to FIG. 2, depicted is an aspect of the device for perfusion management 100 which includes the body portion 102 from which a set of at least one arm 104 projects. In one aspect, each of the at least one arm 104 is in fluid communication with a respective receptacle 106. Each receptacle 106 may be filled with a different fluid for delivery. In another approach, the one or more receptacles 106 may be coupled to a mixing chamber where the fluid contents of each receptacle 106 are present for mixing and the mixed contents enter the arm for delivery to a selected location. The choice of fluid in the receptacle 106 may depend, for example, on the purpose of the device, for example, treatment of colon cancer, treatment of breast cancer, or treatment of an arterial disease. The choice of fluid in the receptacle 106 includes, but is not limited to, for example, a chemical, a chemical compound, a protein, a lipoprotein, a glycoprotein, a sugar, a lipid, an antigen, an antibody, a cytokine, a peptide, a neurotransmitter, a hormone, an ion, a messenger a molecule, a nucleic acid, an engineered nucleic acid, a nucleic acid vector, a drug, a cell, a cell fragment, a cell organelle, a liposome, a pharmaceutical agent, a biological material, or a biological fraction. The receptacle 106 may also be utilized for storage and disposal of operational fluids. Also, although the exemplary embodiment described herein focuses primarily on fluid delivery, one skilled in the art will understand that fluid-like substances, such as gels, and fluidizable substances or non-fluid type substances, such as small solid particles, may be delivered in accordance with the invention. It will also be appreciated by those having skill in the art that the nature of the fluid in the receptacle 106 includes, for example, and is not limited to, a liquid, a solution, a mixture, a gel, a colloid, a colloid of a suitable viscosity, a suspension, an emulsion, or any material of low shear-strength for delivery to a site.

In one aspect one or more fluids are delivered to one or more of selected locations by the device for perfusion management 100. The selected location may be, for example, in proximity to or within a tumor, a circulatory system, an aorta, a vena cava, a site of therapy, or a site of investigation in an animal.

Continuing to refer to FIG. 2, a pump 218 provides fluid at a controlled flow rate for delivery to a site from the receptacle 106. It will be appreciated by those skilled in the art that the type of pump is not critical to the invention and may include, for example, a mechanical pump, a piezoelectric pump, an osmotic pump, a source of pressure, or a device for maintaining a positive flow of fluid through the device. Additionally, fluid flow may be further modulated with micro valves and self-pressurizing fluidic reservoirs. Moreover, in some applications, the fluid may be delivered without a pump. For example, fluid delivery may be controlled using a pressurized bladder, controlled dissolution or dilution of a material, a drip or gravity type of approach, or any other suitable approach to deliver an appropriate amount or an appropriate delivery-rate of the fluid.

With reference now to FIG. 3, depicted is an exploded view of the arm 104 showing a plurality of extended parts 304 with the sensor 116 at the distal end of each of the extended parts 304. In one aspect of the invention, the sensor 116 is an array of sensors, deployed from one or more portholes, at the distal end of each of the extended parts 304. In one approach, the portholes are sized and shaped to provide access through which the sensors 116 may be deployed. The portholes may include seals, stress relief or other features appropriate for proper mechanical deployment. In one approach, one or more of the portholes can be controllably opened or closed to provide communication exterior to the arm or main body. The sensor 116 may be retracted within the porthole and deployed through the porthole. Where the porthole can be opened and closed, the porthole can close to limit communication and can be opened for deployment. The array of sensors may include, but is not limited to, for example, sensors for detecting pressure, temperature, chemical, gas, electrolyte, flow, volume, composition, or concentration. In an alternate aspect of the invention, microelectrodes, such as, for example, solid-state microelectrodes, are sensitized with an agent for detecting a relevant interacter. Examples of the agent include, but are not limited to, for example, agonists of angiogenesis. The choice of sensor 116 depends on the physiological variable being monitored, treated, or controlled. The term "physiological variable" refers to any and all measurements relating to the functioning of a living organism in normal, sub-normal, or abnormal states.

Figure 4:
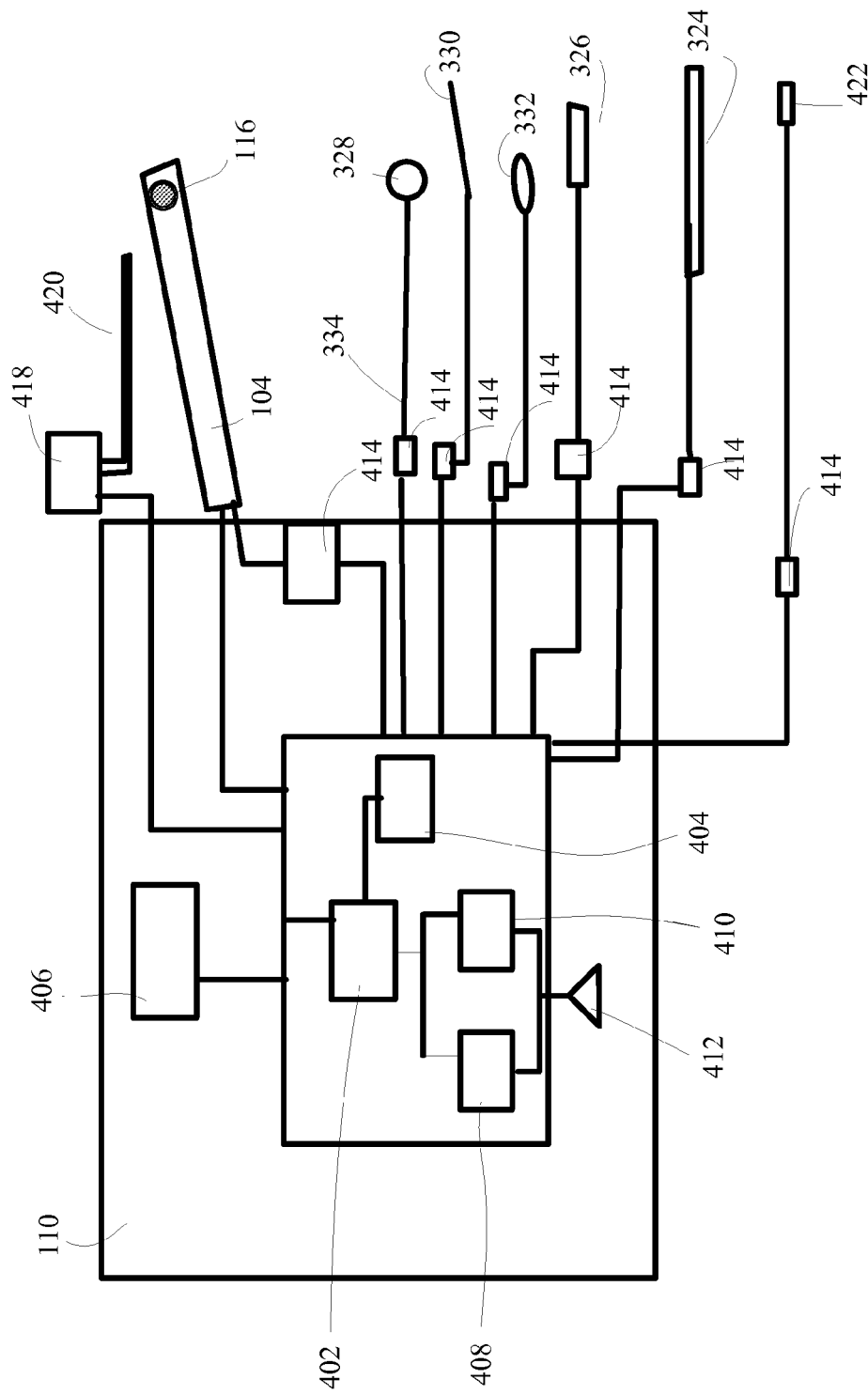
FIG. 4 is a schematic view of the control circuit 110 and devices in communication with the control circuit 110.

Continuing to refer to FIG. 3 and referring now to FIG. 4, an operative tool 324 is coupled to the distal most extended part 304, or deployed from the porthole, or carried by the arm 104, further including a carrying line 334 in communication with the control circuit 110. The operative tool 324 includes, but is not limited to, for example, one or more of a combination of, a tool positioner, an ablation device, a laser, a vacuum, a siphon 326, an evacuation device, a fluid dispenser 328, a cauterizer 330, a stent 332, a tissue-liquefying device, or a source of an electric charge or electromagnetic radiation 422. The vacuum or the siphon 326 is employed for removing a cell, a mass of cells, a tissue, a fluid, a gel, a sample, a debris, a contaminant, or other material for which removal is desired or appropriate. The ablation device operates for perturbing or reducing the structural integrity or viability of a cell, a mass of cells, an assembly of biological materials exhibiting shear strength, or a tissue. The assembly of biological materials includes, for example, blood clots, cartilage, or bone. The source of an electric charge or electromagnetic radiation 422 includes, but is not limited to, for example, steady state electric currents, time-varying electric currents, alternating electric currents, radio waves, microwaves, ultraviolet rays, infrared rays, optical rays, terahertz beams, and the like.

Continuing to refer to FIG. 3, it will be appreciated by those having skill in the art that the operative tool 324 may include a set of devices having general or "multi-purpose" utility. The operative tool 324 may include, but is not limited to, for example, a combination of the fluid dispenser 328, the siphon 326, and the ablation device. In this example the operative tool combination, for example, delivers the fluid or gel, ablates cells, and removes debris.

Continuing to refer to FIG. 3, the plurality of extended parts 304 may themselves be hollow forming a conduit for delivery of the fluid to a site, or for housing a circuitry coupling the control circuit 110 to the operative tool 324, or for housing a mechanism that guides the arm 104 or the plurality of extended parts 304.

With reference now to FIG. 4, illustrated is a schematic view of the control circuit 110 and devices in communication with the control circuit 110. The device for perfusion management 100 shows a data transmitter 410, and a data receiver 408 coupled to the control circuit 110. An antenna 412 may be used for transmitting data to the exterior wirelessly. The antenna 412 is shown diagrammatically, but may be a structure, such as a strip antenna, that may be integrated in a manner that does not impair or significantly perturb system performance. The control circuit 110 is depicted as having a processor 402 coupled to a memory 404 that provides data storage and retrieval capability, and a power source 406. Feedback circuitry or logic circuitry provides communication between the control circuit 110 and devices in communication with it. In some applications, a software program providing instructions may be stored in the memory 404 to control operation of the control circuitry or to store data gathered under control of the control circuitry. Additionally, the control circuit 110 may have components for system integrated digital data gathering, processing, storage, compression and transmission. These can provide data control capabilities and operation control capabilities. For example, the transmission components may communicate through the antenna 412 to a person, system, computer, or device exterior to the body. This communication can allow data gathered by the sensors to be displayed, stored or otherwise processed in the external environment. Additionally, this communication may allow for the processed data or a plurality of new data to be received from the exterior by the device for perfusion management 100. Data compression can allow the control circuitry to store data representing larger amounts of data to be stored in the memory 404 or to be transmitted to the exterior environment in a more efficient manner.

Continuing to refer to FIG. 4, one or more of the operative tools 324 are mounted on an actuator 414 which allows for the independent movement of each tool. Alternatively, one or more operative tools 324 may be mounted as a unit on one actuator 414 and moved as a group, for example, forming an aspirating-dispensing unit. For example, the fluid dispenser 328 and the siphon 326 may be mounted together as a group. The actuator 414 may be a motor, a piezo electrically driven actuator, a micromechanical or electrical effector, or the like.

Continuing to refer to FIG. 4, the arm 104 may include an imaging device deployed from the porthole or from the distal end of the arm 104 or carried by a carrying line 334. The term "imaging device" being used herein to designate in general those components, circuits, assemblies and sub-assemblies comprising electrical, optical, acoustic, or opto-electronic components. In one aspect, the control circuit 110 is coupled to the imaging device that includes a laser 418, or a source of light or scene-illuminating radiation, coupled to an optical feed line 420 to illuminate an area. A charge coupled device is positioned to capture data from the illuminated area and provides an electronic signal indicative of the area imaged. Conventional circuitry then produces a digital representation that may be displayed, stored in the memory 404, or otherwise processed. The displayed image may serve, for example, for guiding the arm 104 to the selected location or for determining the efficacy of a treatment or a procedure. One skilled in the art will recognize that the imaging device described herein is exemplary of imaging devices and that other imaging devices, including for example, raster and line-scanning imagers, nonvisible spectral imagers, and fluorescence imagers, may be included.

Figure 5:
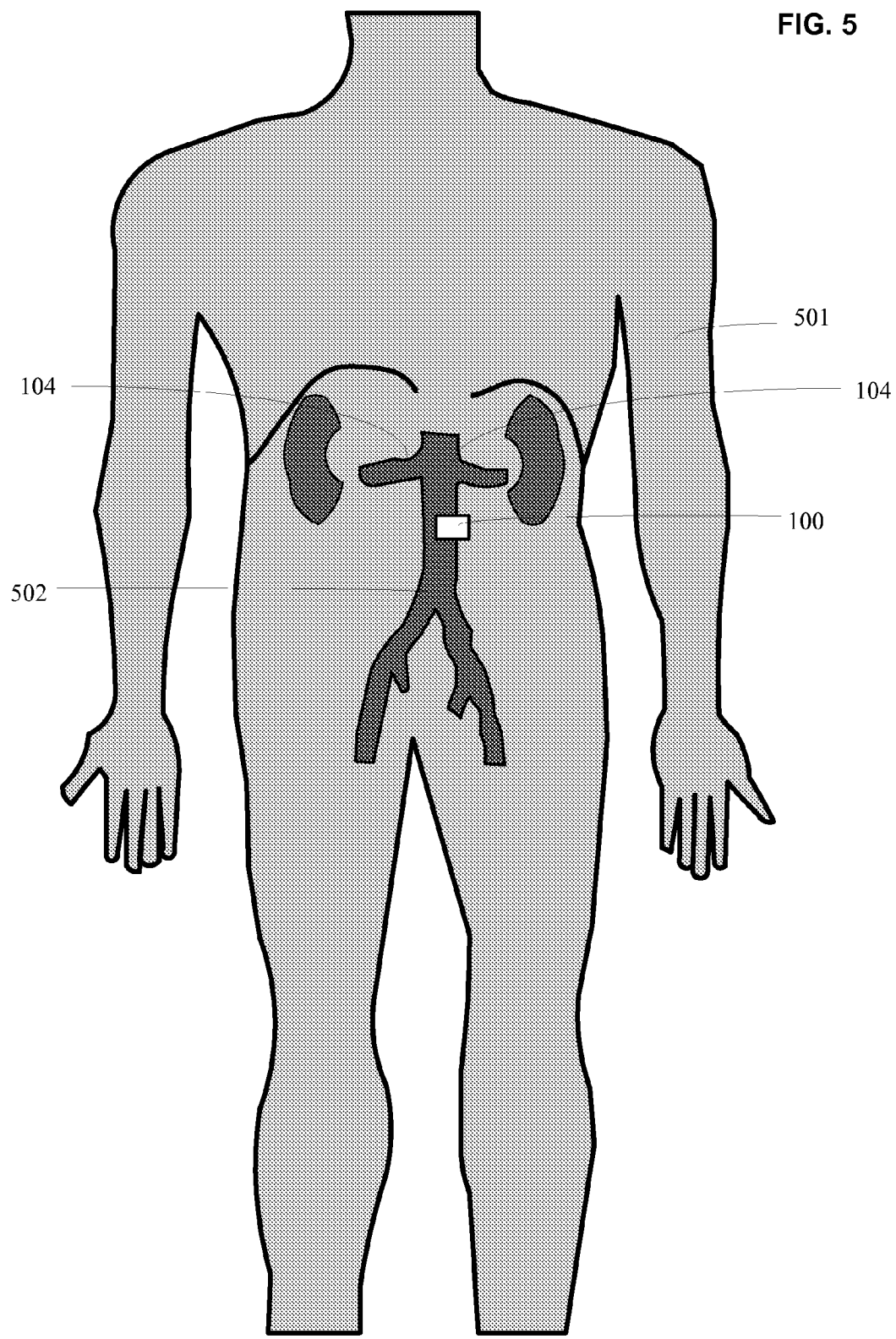
FIG. 5 illustrates an example wherein the device for perfusion management 100 is placed in a selected location in a human body 501.

With reference now to FIG. 5, the device for perfusion management 100 is depicted implanted in an aorta 502 with the arm 104 traveling a blood vessel in a human body 501. Additionally, the device for perfusion management 100 is configured for full or partial placement in the human body 501. The configuration may incorporate a combination of the following criteria, including but not limited to, dimensions, composition, shape, power dissipation level, or texture. In one aspect, the body portion 102 is sized for implantation in proximity to the aorta 502 or the vena cava and the arm 104 is sized for traveling a blood vessel in an animal, for example, the human body 501. In this aspect, if the vasculature decreases two-fold, each of the extending parts 304 has about a two-fold decrease in diameter. The length of the arm 104, for example, depends upon the distance between the selected location and the location of the body portion 102, and the route traveled by the arm 104 to arrive at the selected location. It will be appreciated by those having skill in the art that the arm 104 including the one or more of the operative tools 324 is of a size, dimension or shape operable for traveling one or more blood vessel of decreasing or increasing luminal diameter. It will also be appreciated by those having skill in the art that the arm 104 and the one or more operative tool 324 may pass through the wall of a lumen, or trans-luminally, to the surrounding tissue for detecting, delivery of a treatment, or for sampling. It will also be appreciated by those having skill in the art that the trans-luminal mode described is not limited to blood vessels and includes the space or cavity of an organ or structure.

It will also be appreciated by those having skill in the art that the device for perfusion management 100 and its components, such as, for example, the arm 104, the plurality of extended parts 304, or one or more operative tools 324, has a size, dimension, shape, material, and properties of flexion, retraction, and extension to allow for the steering, guiding, or positioning of the components of the device for perfusion management 100. For example, the arm 104 may need to be steered around an occlusion or a fork in the vasculature. In this example, the arm 104 may need to retracted, repositioned and then extended in a new direction. Extending, retracting or repositioning of the arm 104 may be accomplished by techniques known in the art, for example, by using a guide wire or a by employing a shape polymer. In another aspect, the arm may be retracted and then "punched through" an occlusion to dislodge, penetrate, or grapple it. In this example, a laser beam, a shearing tool, a cutting tool, or a drug, for example, a lytic drug, may be employed to degrade or reduce the occlusion. In this example, subsequent to the dislodgement and degradation of the occlusion, the siphon 326 or an evacuation device is employed to evacuate any debris, before the arm 104 continues traveling the circulatory system. It will also be appreciated by those skilled in the art that the device for perfusion management 100 is not restricted to traveling the circulatory system but may be implanted in any tissue, such as, for example, nerve, epithelial, dermal, sub-dermal, connective, or muscle tissue. Additionally, the device for perfusion management 100 may be implanted in inter-tissue spaces, or inter-organ spaces, for example, those found within a body cavity.

In one aspect the device for perfusion management 100 includes an array of sensors 116 positioned across the plurality of extended parts 304 for monitoring, tracking, or mapping a gradient of temperature, pressure, flow, or material concentration in one or more locations. The one or more locations may be, for example, a tissue, an artery, or a vein. In another aspect the device for perfusion management 100 has an auto-correct feature for correcting a sub-normal or abnormal gradient of temperature, pressure, flow, or material concentration. In yet another aspect the device for perfusion management 100 has an auto-correct feature for detecting and correcting a sub-normal or abnormal gradient of temperature, pressure, flow, or material concentration.

The device for perfusion management 100 may be composed of materials known in the art, for example, a metal, a ceramic, a glass, a plastic, a polymer, a biologically compatible material, or a combination. For example, the device for perfusion management 100 may be made of helically-coiled stainless steel wire and coated with a polymer, such as, Teflon™. In another example, the device for perfusion management 100 may be made of helically-coiled stainless steel wire and coated with a polymer and impregnated with one or more of a biological material, for example, including but not limited to, anti coagulants, or inhibitors.

B. Operation(s) and/or Process(es)

Those having skill in the art will appreciate that some or all of the components of the device for perfusion management 100 may be present ex vivo. In one implementation, the device for perfusion management 100 is placed in proximity to the location on the animal, for example, the human body 501, and the at least one arm 104 directed to the selected location and an effective agent delivered in proximity to the selected location. The arm 104 may be retracted after such a delivery, leaving the device for perfusion management 100 in place at the location, until time for a future delivery of the effective agent or another procedure or operation. In this implementation, the majority of the device for perfusion management 100 is ex vivo while the arm 104 alternates between ex vivo and in vivo states.

In another aspect, some or all the components of the device for perfusion management 100 are present in vivo. In one implementation, the device for perfusion management 100 is placed in proximity to the location within the animal, for example, the human body 501, and the arm 104 directed to a selected location and an effective agent delivered in proximity to the selected location. The arm 104 may be retracted after such a delivery, leaving the device for perfusion management 100 in place at the location, until time for a future delivery or another operation. In this implementation, the majority of the device for perfusion management 100 is in vivo while the arm 104 alternates between retracted, partially retracted or unretracted states.

In one implementation, the device for perfusion management 100 is operable by a person. The person monitors, guides, positions, and performs other actions/operations or manages a response consistent with the device for perfusion management 100 being managed by the person. In such an implementation a separate display device can present imagery to aid the person. The imagery may be captured as described above with reference to FIG. 4, may be computer generated or may be captured by a separate imaging device internal to or external to the animal, for example, the human body 501. Actions may be performed under control of the person who may be on site or may be linked from a remote location, or the device for perfusion management 100 may be programmed to perform some or all functions automatically. For example, the device for perfusion management 100 may be programmed to perform functions, such as, lumen clearance, lumen maintenance, monitoring of concentrations, sending of alerts, delivery of one or more of the effective agent at timed intervals or locations, self-check, or self-diagnosis. It will be appreciated by those of skill in the art that the device for perfusion management 100 may be programmed for complete automatic operation of one or more functions.

C. Variation(s), and/or Implementation(s)

Those having skill in the art will recognize that the present application teaches modifications of the devices, structures, and/or processes within the spirit of the teaching herein. For example, the device for perfusion management 100 need not be limited to managing perfusion. The device provides a mechanism for exploring one or more regions and/or reaching a location within an animal, obtaining information, communicating this information, performing operations, performing procedures, or providing treatment. The treatment includes but is not limited to, for example, treatment of a subnormal, abnormal or pathological condition. In another example, the device for perfusion management 100 may find utility in the management of physiological functions, the detection or elimination of pathological functions or conditions, and/or treatment of a disease or a pathological state of non-human animals. Other modifications of the subject matter herein will be appreciated by one of skill in the art in light of the teachings herein.

The foregoing described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular aspects of the present subject matter described herein have been shown and described, it will be obvious to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is defined solely by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations), etc.

What is claimed is:

1. A device for perfusion management comprising:
    at least one extensible conduit operable to deliver one or more receivables to at least one bodily location; and
    an array of sensors that are distributed along a length of the at least one extensible conduit and that are operable to obtain information associated with two or more positions.

2. The device for perfusion management of claim 1, wherein the at least one extensible conduit is articulatable.

3. The device for perfusion management of claim 1, wherein the at least one extensible conduit is flexible.

4. The device for perfusion management of claim 1, wherein the at least one extensible conduit is retractable.

5. The device for perfusion management of claim 1, further comprising:
    at least one other conduit.

6. The device for perfusion management of claim 1, wherein the at least one extensible conduit is guidable.

7. The device for perfusion management of claim 1, wherein the at least one extensible conduit includes one or more stent portions.

8. The device for perfusion management of claim 1, wherein at least some of the array of sensors are operable to obtain composition information.

9. The device for perfusion management of claim 1, wherein at least some of the array of sensors are operable to obtain image information.

10. The device for perfusion management of claim 1, wherein at least some of the array of sensors are distributed along a length of one or more sidewalls of the at least one extensible conduit.

11. The device for perfusion management of claim 1, wherein at least some of the array of sensors are distributed among two or more segments of the at least one extensible conduit.

12. The device for perfusion management of claim 1, wherein the array of sensors includes three or more sensors.

13. The device for perfusion management of claim 1, further comprising:
    one or more reservoirs operable to contain one or more receivables.

14. The device for perfusion management of claim 1, further comprising:
    one or more mixing units operable to mix one or more receivables.

15. The device for perfusion management of claim 1, further comprising:
    one or more polymers operable to perform one or more actions.

16. The device for perfusion management of claim 1, further comprising:
    one or more tools.

17. The device for perfusion management of claim 16, wherein at least some of the one or more tools are operable to obtain at least some material.

18. The device for perfusion management of claim 16, wherein at least some of the one or more tools are associated with one or more portholes of the at least one extensible conduit.

19. The device for perfusion management of claim 1, further comprising:
    at least one communication unit.

20. The device for perfusion management of claim 1, further comprising:
    at least one source of radiation.

21. The device for perfusion management of claim 1, further comprising:
    at least one source of current.

22. The device for perfusion management of claim 1, further comprising:
    control circuitry configured to signal for delivery of one or more receivables in response to information obtained from at least some of the array of sensors.

23. The device for perfusion management of claim 1, wherein the device is fully implantable.

24. The device for perfusion management of claim 1, wherein the device is at least partially programmably controllable.

* * * * *